US012767627B2

(12) United States Patent
Oren et al.

(10) Patent No.: US 12,767,627 B2

(45) Date of Patent: Oct. 20, 2026

(54) PREPARATION OF CIS-2-ALKENOIC ACIDS

(71) Applicant: BROMINE COMPOUNDS LTD., Beer-Sheva (IL)

(72) Inventors: Jakob Oren, Nesher (IL); Nasif Yassin, Tamra (IL); Nicka Chinkov, Kibbutz Mishmar Haemek (IL); Ronit Yahalomi Segui, Kiryat Bialik (IL)

(73) Assignee: BROMINE COMPOUNDS LTD., Beer-Sheva (IL)

( * ) Notice: Subject to any disclaimer, the term of this patent is extended or adjusted under 35 U.S.C. 154(b) by 633 days.

(21) Appl. No.: 18/039,352

(22) PCT Filed: Nov. 30, 2021

(86) PCT No.: PCT/IL2021/051423

§ 371 (c)(1),
(2) Date: May 30, 2023

(87) PCT Pub. No.: WO2022/118309

PCT Pub. Date: Jun. 9, 2022

(65) Prior Publication Data

US 2024/0002323 A1 Jan. 4, 2024

Related U.S. Application Data

(60) Provisional application No. 63/119,669, filed on Dec. 1, 2020.

(51) Int. Cl.
*C07C 51/02* (2006.01)
*C07C 51/347* (2006.01)

(52) U.S. Cl.
CPC ............ *C07C 51/02* (2013.01); *C07C 51/347* (2013.01); *C07B 2200/09* (2013.01)

(58) Field of Classification Search
CPC ....... C07C 51/02; C07C 51/347; C07C 51/00; C07C 45/63; C07B 2200/09
See application file for complete search history.

(56) References Cited

U.S. PATENT DOCUMENTS 3,385,889 A 5/1968 Christoffer
8,748,486 B2 * 6/2014 Wang ...................... A61P 31/00 514/529
2011/0160304 A1 6/2011 Wang et al.

FOREIGN PATENT DOCUMENTS

WO 2008143889 A1 11/2008
WO 2020240559 A1 12/2020
WO 2023238135 A1 12/2023

OTHER PUBLICATIONS

Rappe et al.: "Favorsky Rearrangements IV. The Preparation of Some cis-alpha,beta-U nsaturated Acids", Acta Chemica Scandinavica, vol. 19, 1965, pp. 383-389. (Year: 1965).*

(Continued)

*Primary Examiner* — Deborah D Carr

(74) *Attorney, Agent, or Firm* — Elmore Patent Law Group, PC; Joseph C. Zucchero; Carolyn S. Elmore

(57) ABSTRACT

A process for the preparation of cis-2-alkenoic acid or an alkali metal salt thereof, comprising rearranging 1,3-dibromo-2-alkanone in an alkaline environment in the presence of a catalytically effective amount of an alkali metal salt of cis-2-alkenoic acid, and isolating from the reaction mixture cis-2-alkenoic acid, either in the form of the free acid or in the form of the alkali metal salt.

14 Claims, 18 Drawing Sheets

$^1$H-NMR spectrum of sample: "300766-23-CDA" in $CDCl_3$ EH.13377.

Zoom of $^1$H-NMR spectrum of sample: "300766-23-CDA" in $CDCl_3$ EH.13377:

(56) References Cited

OTHER PUBLICATIONS

Davies, D. G. et al., “A Fatty Acid Messenger Is Responsible for Inducing Dispersion in Microbial Biofilms”, J. Bacterol., 191(5), doi:10.1128/JB.01214-08, Mar. 2009, 1393-1403.
Rappe, C. , “cis-α,β-Unsaturated Acids: Isocrotonic Acid”, Org. Synth., 53, DOI:10.15227/orgsyn.053.0123, 1973, 123.
Rappe, C. et al., “Favorsky Rearrangements IV. The Preparation of Some cis-alpha,beta-Unsaturated Acids”, Acta Chem. Scand., 19(2), 1965, 383-389.

* cited by examiner

1A: $^{1}$H-NMR spectrum of sample: "300766-23-CDA" in $CDCl_3$ EH 13377:

1B: Zoom of $^1$H-NMR spectrum of sample: "300766-23-CDA" in $CDCl_3$ EH.13377;

1C: Zoom of $^1$H-NMR spectrum of sample: "300766-23-CDA" in $CDCl_3$ EH.13377;

2A: $^1$H-NMR spectrum of sample: "300766-17-CDA" in $CDCl_3$ EH.13293.

2B: Zoom of $^1$H-NMR spectrum of sample: "300766-17-CDA" in $CDCl_3$ EH.13293.

2C. Zoom of $^1$H-NMR spectrum of sample: "300766-17-CDA" in $CDCl_3$ EH.13293.

3A: $^1$H-NMR spectrum of sample: "300766-21-CUDA" in $CDCl_3$ EH.13345;

3B: Zoom of $^1$H-NMR spectrum of sample: "300766-21-CUDA" in $CDCl_3$ EH.13345;

3C: Zoom of $^1$H-NMR spectrum of sample: "300766-21-CUDA" in $CDCl_3$ EH.13345:

4A: $^1$H-NMR spectrum of sample: "300766-31-CNA" in $CDCl_3$ EH.13449:

4B: Zoom of $^1$H-NMR spectrum of sample: "300766-31-CNA" in $CDCl_3$ EH.13449;

4C: Zoom of $^{1}$H-NMR spectrum of sample: "300766-31-CNA" in $CDCl_3$ EH.13449:

5A: $^{1}$H-NMR spectrum of sample: " 300766-32-COA " in $CDCl_3$ EH.13459;

5B: Zoom of $^1$H-NMR spectrum of sample: " 300766-32-COA " in $CDCl_3$ EH.13459:

5C: Zoom of $^1$H-NMR spectrum of sample: " 300766-32-COA " in $CDCl_3$ EH.13459:

6A: $^1$H-NMR spectrum of sample: " 300766-33-CHA " in $CDCl_3$ EH.13462:

6B: Zoom of $^{1}$H-NMR spectrum of sample: " 300766-33-CHA " in $CDCl_3$ EH.13462.

6C: Zoom of $^1$H-NMR spectrum of sample: " 300766-33-CHA " in $CDCl_3$ EH.13462:

PREPARATION OF CIS-2-ALKENOIC ACIDS

RELATED APPLICATIONS

This application is a 371 of International Application No. PCT/IL2021/051423, filed Nov. 30, 2021, which claims the benefit of U.S. Provisional Application No. 63/119,669 filed on Dec. 1, 2020. The entire teachings of the above application(s) are incorporated herein by reference.

The invention relates to the synthesis of long chain cis-α,β-unsaturated acids of the formula R—CH═CH—COOH, i.e., cis-2-alkenoic acids, where R indicates an alkyl residue (linear or branched) consisting of not less than, e.g., 4 carbon atoms.

It has been reported that long chain cis-2-alkenoic acids act as bio-dispersants. For example, it was shown in WO 2008/143889 and the Journal of Bacteriology 191:1393-1403 (2009) that cis-2-decenoic acid, produced by the bacterium *Pseudomonas aeruginosa*, is capable of inducing *P. aeruginosa* and other gram-negative and gram-positive bacteria and fungi to undergo a physiologically-mediated dispersion response, resulting in the dis-aggregation of surface-associated microbial populations and communities known as biofilms.

In co-assigned PCT/IL2020/050591 (≡WO 2020/240559), it was demonstrated that cis-2-decenoic acid can act as an effective adjunctive to bromine-containing biocides in the treatment of biofilm and planktonic bacteria in water systems and on surfaces in contact with the water, to achieve significant enhancement in the killing of bacteria in both pure and mixed cultures typically found in industrial and natural waters, relative to treatment with the brominated biocides alone. Notably, it was shown in PCT/IL2020/050591 that satisfactory enhancement of bromine-based water treatments can be achieved with the aid of cis-2-decenoic acid of moderate purity, say, (by gas chromatography, GC area %).

We have now developed a synthesis of long chain cis-2-alkenoic acids or salts thereof, recovering crude products with acceptable purity levels, suitable for use, without further purification, in bromine-based water treatments.

The synthesis is based on a two-step process consisting of brominating the corresponding 2-alkanone to give crude 1,3-dibromo-2-alkanone as a main product alongside other isomers, followed by rearrangement of the 1,3-dibromo-2-alkanone to the unsaturated acid, depicted by the scheme below:

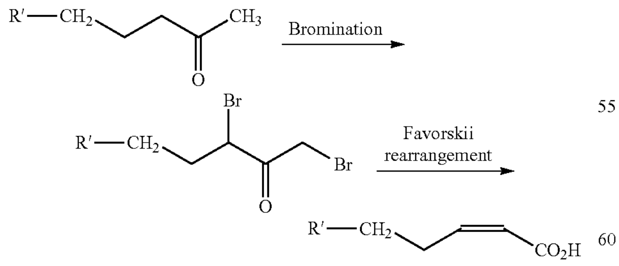

[where R' is alkyl, e.g., $C_2H_5$, $C_3H_7$, $C_4H_9$, $C_5H_{11}$ and $C_6H_{13}$]. The abovementioned two-step synthesis was first described by Rappe et al. [Acta Chemica *Scandinavica* (1965), Vol. 19 p. 383-389]. The rearrangement took place in an alkaline environment, using alkali carbonates or alkali bicarbonates as a base. A similar approach was reported by the same research group in Organic Syntheses (1973), Vol. 53, p.123-127.

An attempt to modify the two-step synthetic pathway is found in U.S. Pat. No. 8,748,486, where it was explained that alkali bicarbonate can only effectively advance the preparation of short chain cis-α,β-unsaturated acids. The authors reported that the rearrangement reaction of a long chain brominated ketone, e.g., 1,3-dibromo-2-decanone, was very slow in the presence of an alkali bicarbonate, and the desired fatty acid was not obtained even after prolonged reaction time. The authors switched to an alkali hydroxide to advance the preparation of long chain cis-α,β-unsaturated acids (the terms "cis-α,β-unsaturated acids" and "cis-2-alkenoic acids" are used interchangeably).

The Experimental results reported below are in line with the observations made in U.S. Pat. No. 8,748,486: rearrangement reactions of long chain 1,3-dibromo-2-alkanones under an alkaline pH barely make any progress, even at high reaction temperatures, and are prone to the occurrence of thermal runaway (a sudden and rapid rise in the reaction temperature). Such a reaction profile is unacceptable for a process running on an industrial scale.

However, it has now been found that a given amount of the alkali salt of the target cis-2-alkenoic acid should be provided in the reaction mixture to advance the rearrangement reaction of the 1,3-dibromo-2-alkanone in an effective and manageable manner, leading to the cis-2-alkenoic acid. The added alkali salt of the cis-2-alkenoic acid can be supplied to the rearrangement reaction from a previous run, as shown below. With the aid of a small amount of cis-2-alkenoic acid or its salt, added at the beginning of the rearrangement reaction, a manageable process is provided.

Accordingly, the invention is primarily directed to a process for the preparation of a cis-2-alkenoic acid [R—CH═CH—COOH] or an alkali metal salt thereof [R—CH═CH—COOM, wherein M is an alkali metal], comprising rearranging 1,3-dibromo-2-alkanone [R—CHBr—C(O)—$CH_2$Br] in an alkaline environment (e.g., generated by an alkali carbonate, or alkali carbonate/bicarbonate mixture) in the presence of a catalytically effective amount of an alkali metal salt of the cis-2-alkenoic acid, and isolating from the reaction mixture the cis-2-alkenoic acid, either in the form of the free acid or in the form of the alkali metal salt (e.g., by separating the reaction mixture into aqueous and organic phases, and working-up the aqueous phase, to recover therefrom the cis-2-alkenoic acid, either in the form of the free acid or in the form of the alkali metal salt).

R is an alkyl group consisting of not less than four carbon atoms, e.g., not less than five carbon atoms, for example, R is C4-C11 alkyl. For example, cis-2-decenoic acid (R is $C_7H_{15}$), in the free acid form, is collected as an oil. On reaction of the so-formed cis-2-decenoic acid with an alkali hydroxide, e.g., KOH, the corresponding potassium salt is obtained as a paste-like solid.

The cis-2-alkenoic acids R—CH═CH—COOH prepared by the invention are preferably linear. That is, R is usually a straight alkyl chain $CH_3$—$(CH_2)_n$— (3≤n, e.g., 3≤n≤10). For example, the preparation of a cis-2-alkenoic acid by the rearrangement reaction of the corresponding 1,3-dibromo-2-alkanone depicted below was studied (but it should be noted that R is not limited to a normal chain, and may be a branched alkyl group, say, iso-alkyl):

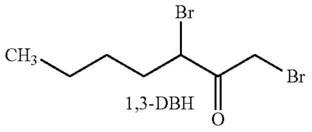
1,3-DBH 1,3-dibromo-2-heptanone

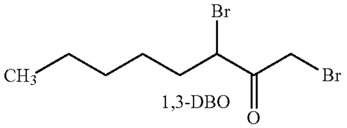
1,3-DBO 1,3-dibromo-2-octanone

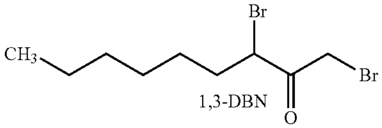
1,3-DBN 1,3-dibromo-2-nonanone

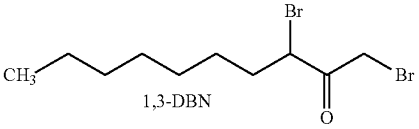
1,3-DBN 1,3-dibromo-2-decanone

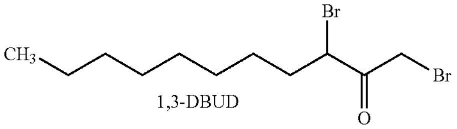
1,3-DBUD 1,3-dibromo-2-undecanone smoothly to the 2-alkanone, with most of the reaction occurring during the addition of the bromine; no bromine accumulation (marked by a characteristic yellow color acquired by the reaction mixture) is observed.

The bromine addition time, on a laboratory scale, is usually from 1 to 5 hours. After the addition of the elemental bromine has been completed, the reaction mixture is held at room temperature (15-25° C.), optionally under stirring, for a period of time ("hold time"). Hold time may last between 6 and 24 hours, e.g., 6 and 12 hours. Long hold times appear to be beneficial because the bromination reaction of 2-alkanone leads to a few isomeric by-products, chiefly 3,3-dibromo-2-alkanone. GC analysis of the reaction mixture indicates that the desired isomer, 1,3-dibromo-2-alkanone progressively becomes the predominant product with the passage of time, i.e., an extended hold time enables a significant interconversion of 3,3-dibromo-ketone to 1,3-dibromo-ketone.

To illustrate the importance of prolonged hold times in shifting the distribution of the isomeric mixture consisting of 1,3-dibromo-2-alkanone and 3,3-dibromo-2-alkanone in favor of the former at the expense of the latter, experimental data is tabulated in Table A, based on the procedures of brominating 2-nonanone, 2-decanone or 2-undecanone (reported in the Working Examples below):

TABLE A

| Hold Time* | Composition**, by GC, area % | | | | | |
|---|---|---|---|---|---|---|
| | Brominating 2-nonanone in HBr | | Brominating 2-decanone in HBr | | Brominating 2-undecanone in HBr | |
| h | 1, 3-DBN | 3,3-DBN | 1,3-DBD | 3, 3-DBD | 1, 3-DBUD | 3, 3-DBUD |
| 0.1-0.5 | 42.8 | 27.5 | 47.5 | 26.6 | 48.1 | 26.0 |
| 2.0-2.5 | 60.3 | 21.4 | 59.9 | 13.6 | 55.9 | 17.9 |
| 20-21 | 70.6 | 6.3 | 69.6 | 5.8 | 69.4 | 6.2 |

*Time elapsed after completion of the bromine addition at TR ~20° C.

**Other impurities consisting of 3-bromo-2-alkanone and isomers of tribromo-2-alkanone are also present and all were found to benefit from the addition of a catalytically effective amount of the target cis-2-alkenoic acid or its alkali metal salt to the alkaline reaction mixture. By "catalytically effective amount", it is meant that the added amount is up to 15 mol %, e.g., up 10 mol %, e.g., from 1 to 5 mol % based on 1,3-dibromo-2-alkanone.

The 1,3-dibromo-2-alkanone undergoing the rearrangement reaction is most conveniently prepared by brominating the corresponding 2-alkanone [R—$CH_2$—C(O)—$CH_3$] (e.g., 2-heptanone, 2-octanone, 2-nonanone, 2-decanone or 2-undecanone) in concentrated hydrobromic acid (e.g., from 30% to 48% by weight HBr solution), by the slow addition of elemental bromine (stoichiometry dictates a ~2:1 molar ratio of $Br_2$: 2-alkanone).

The weight ratio of the 2-alkanone starting material to the aqueous HBr is of 1:1 to 1:2. The reaction medium is chilled to a temperature in the range from 5 to 20° C. e.g. around 5 to 10° C. Under these conditions, elemental bromine adds It is seen that the product mixtures obtained by brominating various 2-alkanones in hydrobromic acid behave in a similar manner on standing over long hold times. Initially, the mixture consisting of 1,3-dibromo-2-alkanone and 3,3-dibromo-2-alkanone is proportioned ~2:1; after ~twenty hours, the proportion is higher than 10:1, with the equilibrium stabilizing and reaching ~70% (GC, area %) of the desired isomer which is amenable to the rearrangement reaction, i.e., the 1,3-dibromo-2-alkanone.

Evolution of hydrogen bromide occurs during the bromine addition and subsequent hold phases; the gas is absorbed in a suitable aqueous medium, to be collected as aqueous hydrobromic acid.

To recover the crude 1,3-dibromo-2-alkanone, the reaction mixture is worked-up by the addition of water, followed by separation into an aqueous phase (consisting of ~48% w/w hydrobromic acid) and an organic phase, consisting of the crude product. Typically, as indicated by the data tabulated in Table A, the crude product recovered contains ~70% (GC, area) of the 1,3-dibromo-2-alkanone.

Accordingly, in a preferred variant of the invention, the 1,3-dibromo-2-alkanone used in the rearrangement reaction is a crude 1,3-dibromo-2-alkanone obtained by the steps of: brominating the corresponding 2-alkanone in concentrated hydrobromic acid by the addition of elemental bromine, whereby 1,3-dibromo-2-alkanone is formed in the reaction mixture alongside 3,3-dibromo-2-alkanone;

maintaining the reaction mixture over a hold time adjusted to maximize the interconversion of 3,3-dibromo-2-alkanone to 1,3-dibromo-2-alkanone (e.g., to reach >65%, >67%, >69% (GC, area %) of 1,3-dibromo-2-alkanone); and collecting the crude 1,3-dibromo-2-alkanone.

The crude 1,3-dibromo-2-alkanone, without further purification, can now proceed to the rearrangement reaction. However, the invention is not limited to the rearrangement of 1,3-dibromo-2-alkanone obtained by brominating a 2-alkanone in concentrated hydrobromic acid; other methods for the preparation of 1,3-dibromo-2-alkanones reported in the literature may be used, e.g., brominating a 2-alkanone in an organic solvent such as halogenated hydrocarbon ($CH_2Cl_2$ or $CH_2Br_2$) with the aid of acceptable bromination reagents.

A convenient way to carry out the rearrangement reaction comprises gradually adding the 1,3-dibromo-2-alkanone to a reaction vessel which was previously charged with an alkaline aqueous solution (e.g., consisting of 10 to 30% w/w $Na_2CO_3$, $K_2CO_3$ or a mixture thereof dissolved in water, or carbonate/bicarbonate mixtures) and a catalytically effective amount of an alkali metal salt of cis-2-alkenoic acid, at elevated temperature, e.g., 35° C., for example, 40° C., e.g., the gradual addition of the 1,3-dibromo-2-alkanone takes place when the reaction mixture is held at a temperature in the range of 40° C. to 60° C. The molar ratio of 1,3-dibromo-2-alkanone added to the carbonate is from 1:2 to 1:4, e.g., around 1:3-1:3.5.

The use of potassium carbonate, for example, is preferred over sodium carbonate because, as shown below, the corresponding alkali bicarbonate is a by-product of the rearrangement reaction. Less difficulties are likely to be encountered at the work-up stage of the reaction mixture when potassium salts are used, owing to the higher solubility of potassium bicarbonate in water, compared to sodium bicarbonate.

In the presence of an alkali metal salt of the cis-2-alkenoic acid, the reaction takes place during the addition of the 1,3-dibromo-2-alkanone to the alkaline reaction mixture. The occurrence of the reaction is marked by pH drop, (i.e., the initial, strongly alkaline pH of 12-14 drops by at least 2 pH units, e.g., 2-4 pH units, during the addition of the 1,3-dibromo-2-alkanone), and by temperature rise (i.e., $\Delta T_{reactor}$) of ~5 to 10° C.

In contrast, if the 1,3-dibromo-2-alkanone is added to the alkaline solution in the absence of an alkali metal salt of cis-2-alkenoic acid, then the rearrangement of the 1,3-dibromo-2-alkanone progresses poorly, with said added 1,3-dibromo-2-alkanone accumulating in the reaction vessel. The experimental results shown below indicate that the rearrangement of 1,3-dibromo-2-heptanone, 1,3-dibromo-2-octanone and 1,3-dibromo-2-nonanone did not occur during the addition of the crude 1,3-dibromo-2-alkanone. Only after the addition of the crude 1,3-dibromo-2-alkanone has been completed, the pH started to go down and the $T_R$ (reactor temperature) started to go up spontaneously, marking the advance of the reaction. Rearrangement of higher homologues, e.g., 1,3-dibromo-2-decanone and 1,3-dibromo-2-undecanone, is more difficult to advance; and practically no progress can be achieved without the help of a catalytically effective amount of an alkali metal salt of the cis-2-alkenoic acid.

After the slow addition of the crude 1,3-dibromo-2-alkanone has been completed (on a laboratory scale, this may last from 30 to 120 min), the reaction mixture is held under stirring for some time, i.e., a cooking period over a few (1-3) hours, at a temperature in the range from 50 to 55° C., for the reaction to reach completion. A pH drop of ~0.5-1.5 units is observed during the cooking period. The progress of the reaction can be monitored by pH measurement (a constant pH indicates the end of the reaction) and/or GC analysis of the organic phase (to determine the disappearance of the 1,3-dibromo-2-alkanone, i.e., down to 1%, area %).

On completion of the rearrangement reaction, the reaction mixture is cooled to room temperature and separated into aqueous (heavy) and organic (light) phases. The organic phase can be discarded (it contains unreacted brominated isomers which accompanied the 1,3-dibromo-2-alkanone, chiefly 3-bromo-2-alkanone and 3,3-dibromo-2-alkanone; and some condensation by-products formed during the rearrangement reaction). The aqueous phase, which contains the cis-2-alkenoic acid in the form of its alkali metal salt (namely, sodium or potassium salts, determined by the base selected) is worked-up to isolate the product.

One exemplary rearrangement reaction is illustrated by the scheme depicted below, transforming 1,3-dibromo-2-decanone (1,3-DBD) using $K_2CO_3$ into the potassium salt of cis-2-decenoic acid (abbreviated CDA-K):

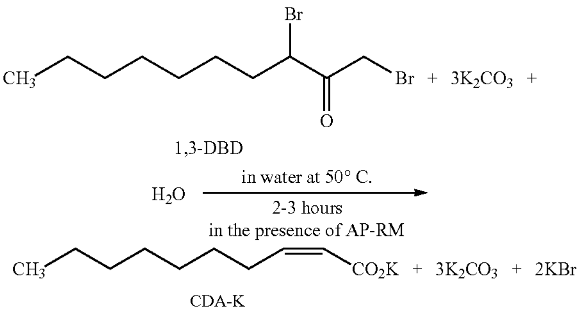

AP-RM indicates the catalytically effective amount of the alkali metal salt of cis-2-alkenoic acid, added in advance to start up the rearrangement reaction. As pointed out above, the catalytically effective amount of the alkali metal salt of the cis-2-alkenoic acid is supplied to the reaction in an aqueous form, for example, by removing a relatively minor portion of the aqueous phase which was collected after the phase separation, and keeping this minor portion for addition in the next run of the process. Usually, the minor portion constitutes from 1 to 10% by weight, e.g., from 3 to 7% (around 5%) of the total weight of the aqueous phase. Based on the concentration of the alkali metal salt of the cis-2-alkenoic acid, it may be appreciated that the catalytically effective amount of the added salt in the alkaline solution before the rearrangement reaction starts is preferably from 1 to 5 molar percent relative to the 1,3-dibromo-2-alkanone.

It should be mentioned, however, that there are alternative ways to supply an alkali metal salt of cis-2-alkenoic acid to the rearrangement reaction, e.g., by the direct addition of the free acid or salt from other sources (if a free acid is added instead of the alkali metal salt, the acid reacts in the alkaline solution to form in situ the corresponding alkali salt).

Next, the major portion of the aqueous phase is worked-up, by washing (repeated washing cycles may be needed) with a water-immiscible organic solvent such as a halogenated hydrocarbon, e.g. dichloromethane, to extract and remove organic impurities from the product-containing aqueous solution.

When the as-obtained reaction mixture cannot be separated into aqueous and organic phases, then it is (optionally) diluted with water and washed with a water-immiscible organic solvent, followed by phase separation, to collect the product-containing, purified aqueous phase, which can be divided into minor and major portions as described above. The minor portion is dedicated to the next run, whereas the major portion is treated to recover the product therefrom.

To recover the product in the form of the free acid, the purified aqueous solution is acidified, e.g., with the aid of concentrated hydrochloric acid (for example, commercially available 32% HCl solution), which is slowly added to the aqueous solution to reach a strongly acidic pH (e.g., from 1 to 2). The acidified reaction mixture is separated into aqueous (heavy) and organic (light) phases. The former contains bromide and chloride salts; the latter consists of the crude cis-2-decenoic acid, and possibly some residual organic solvent which served in the washing stage, and water, which are removed, e.g., by evaporation under vacuum, whereby the crude cis-2-alkenoic acid is obtained.

The sequence of reactions taking place upon acidification of the aqueous solution (specifically, in the preparation of the potassium salt of cis-2-decenoic acid) are shown below:

(1)

$$3KHCO_3 + 3HCl \longrightarrow 3KCl + 3CO_2\uparrow + 3H_2O$$

(2)

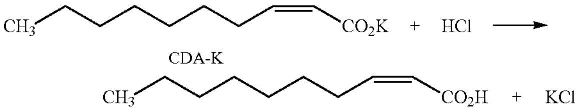

CDA-K

CDA

Accordingly, the process of the invention further comprises the acidification of the purified aqueous phase (i.e., after the extraction with the organic solvent) to obtain biphasic medium, comprised of a heavy, salt-containing aqueous phase, and a light organic phase consisting essentially of the cis-2-alkenoic acid in the form of the free acid.

The corresponding alkali salts can be prepared by conventional methods, e.g., by reacting the free acid with potassium hydroxide in a suitable solvent and separating by crystallization and filtration, followed by drying.

As pointed out above, crude cis-2-alkenoic acids afforded by the process of the invention require no further purification, i.e., the acids are pure enough to act as bio-dispersants in bromine-based water treatments, i.e., their purity levels are >80%, >85%, >87%, e.g., from 80 to 95% (by GC, area %).

Characteristic purity levels of the crude acids are tabulated in Table B below. However, if needed, the crude acid can be purified by conventional techniques, e.g., chromatography or distillation.

TABLE B

| crude cis-2-alkenoic acid | Purity GC, area % |
|---|---|
| 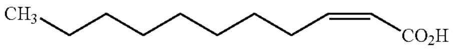 (CUDA) | 89-90 (89.6) |
| 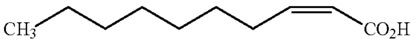 (CDA) | 87-89 (88.2) |
| 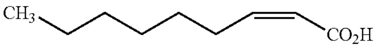 (CNA) | 91-93 (92.0) |
| 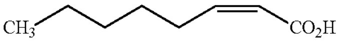 (COA) | 88-90 (89.6) |
| 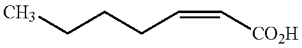 (CHA) | 94-96 (95.6) |

In the Drawings

EXAMPLES

Methods

GC: Gas-Chromatograph HP 7890A

Figure 1A:
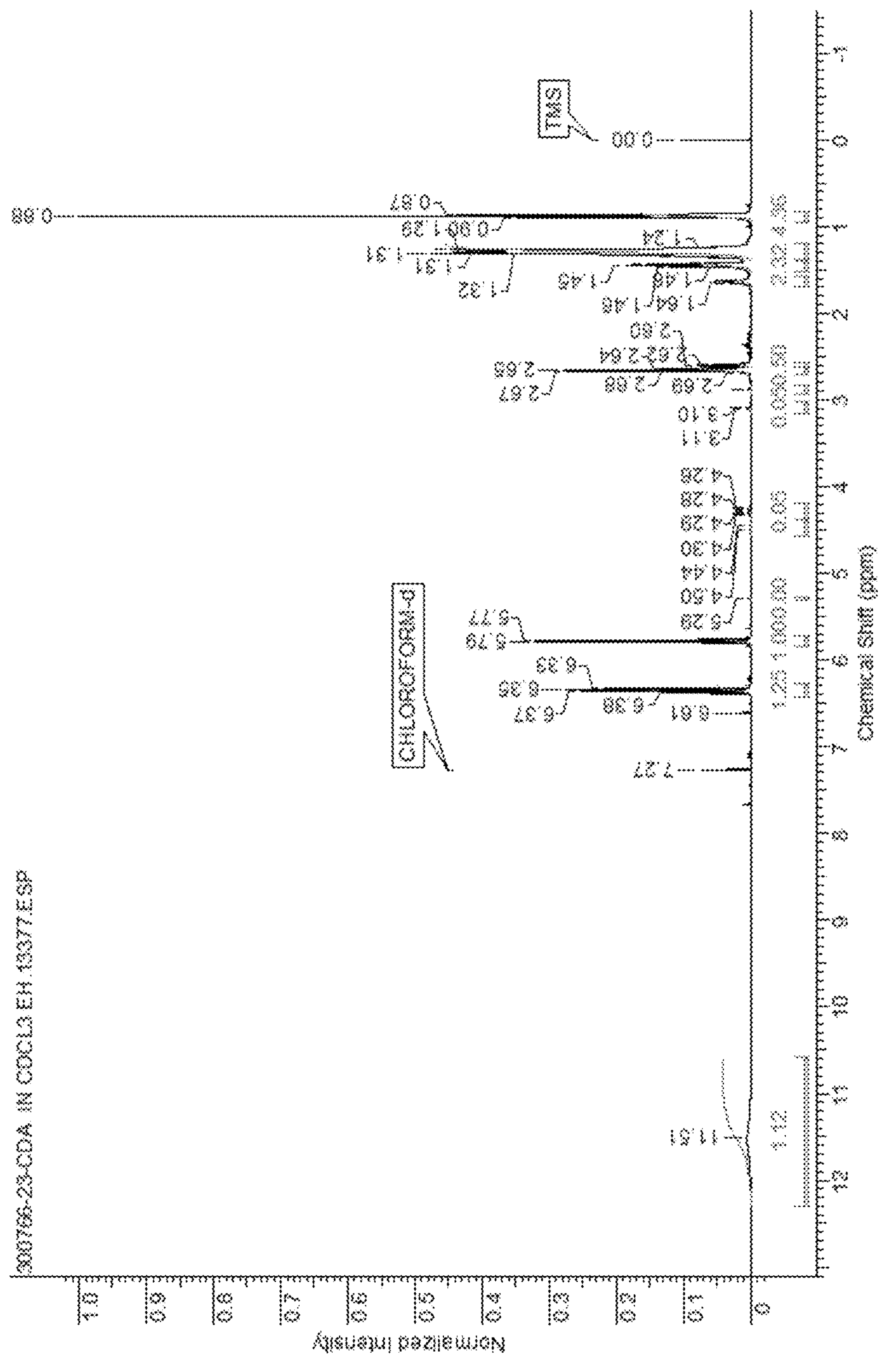
FIGS. 1A, 1B and 1C are $^1$H-NMR spectra of CDA of Example 1.

Method (CDA): Initial temp. 50° C., held 2 min, then raised to

280° C. at 10° C./min and held for 5 min, then raised to 300° C. at

10° C./min and held for 2 min.

Injector: 250° C.

Detector: 300° C.

Split ratio: 1:40

Concentration of the product sample: ~20 mg/ml DCM

Injection amounts: 1 μl sample

Column: Agilent J&W Columns, HP-5, 30 m×0.32 mm×0.25μ

Part no. 19091J-413, Ser. No. USF302346H $^1$H-NMR Spectroscopy

Spectra were taken on an Avance III, 500 MHz instrument.

Example 1

Preparation of Cis-2-Decenoic Acid

Step 1:

Into a mixture of 2-decanone (200 g, 1.28 mol) and aq. 48% HBr (300 g), stirred and cooled to ~10° C., was added bromine (410 g, 2.56 mol), dropwise over 2 h. The reaction started immediately with the start of the addition of the bromine and no accumulation of bromine was observed.

The reaction was exothermic and accompanied by the emission of HBr gas, just before the end of the addition of the bromine, which was absorbed in a scrubber.

Most of the reaction took place during the addition of the bromine and cooking at room temperature (~20° C.) for 6 hours.

After standing overnight (~15 h) at room temperature, without stirring, the composition of the reaction mixture stabilized. Partial conversion of the 3,3-dibromo-2-decanone (3,3-DBD) to the desired product, 1,3-dibromo-2-decanone (1,3-DBD), took place. To the reaction mixture was added water (160 g) at RT, with stirring for 30 min, and the phases were separated.

An aqueous phase (627 g) was obtained containing ~50% HBr (d=1.51 g/ml) and crude DBD (404 g, d=1.43 g/ml). The concentration of 1,3-DBD in the crude product was 69.6% (GC, area %).

Step 2:

An aqueous solution of $K_2CO_3$, in a concentration of 25% w/w, was prepared in a 1 L stirred reactor by the batchwise addition of $K_2CO_3$ (200 g) to water (600 g). The reaction was exothermic. To this solution was added a part of the aqueous phase (which contained CDA-K) of the reaction mixture (50 g) remaining from a previous run (named AP-RM; see comparative Example 3). The clear solution obtained was heated to 40° C. and crude DBD of step 1 (200 g) was added to it dropwise over 60 min. The progress of the reaction was monitored by GC and by the change in the pH. The reaction was completed by cooking at 50° C. for 3.0 h, with mechanical stirring.

It should be pointed out that without the addition of AP-RM, the reaction only starts spontaneously two hours after the addition of the crude DBD.

The end of the reaction was determined by the pH (drop in the pH from 13.3 to 9.3) and by GC analysis of the reaction mixture (disappearance of 1,3-DBD to ≤1%, area %). After completion of the reaction, cooling to RT and stopping the stirring, an organic phase appeared above the aqueous phase which contained unreacted 3-bromo-2-decanone (3-BD) and 3,3-DBD, and by-products formed by a condensation reaction of crude DBD. The phases were separated. The organic phase (39 g) was organic waste. 50 g of the aq. phase was taken for use in the next run.

In order to reduce the amount of impurities to a minimum, the remainder of the aqueous phase (950 g) was washed three times with dichloromethane (DCM, 3×250 g).

After the washing stage, an aqueous phase was obtained containing cis-2-decenoic acid potassium salt (CDA-K), organic by-products, KBr and $KHCO_3$. In order to obtain the crude cis-2-decenoic acid (CDA), the aqueous phase was acidified by the dropwise addition of aq. 32% HCl (193 g) over 1 h. During the acidification (final pH=1.1), $CO_2$ (calculated at 63 g) was emitted.

After stopping the stirring, an aqueous phase (955 g) was obtained containing salts: KCl and KBr (heavy phase, d=1.19 g/ml) and wet crude CDA (light phase, 71 g, d=1.07 g/ml).

Figure 1B:
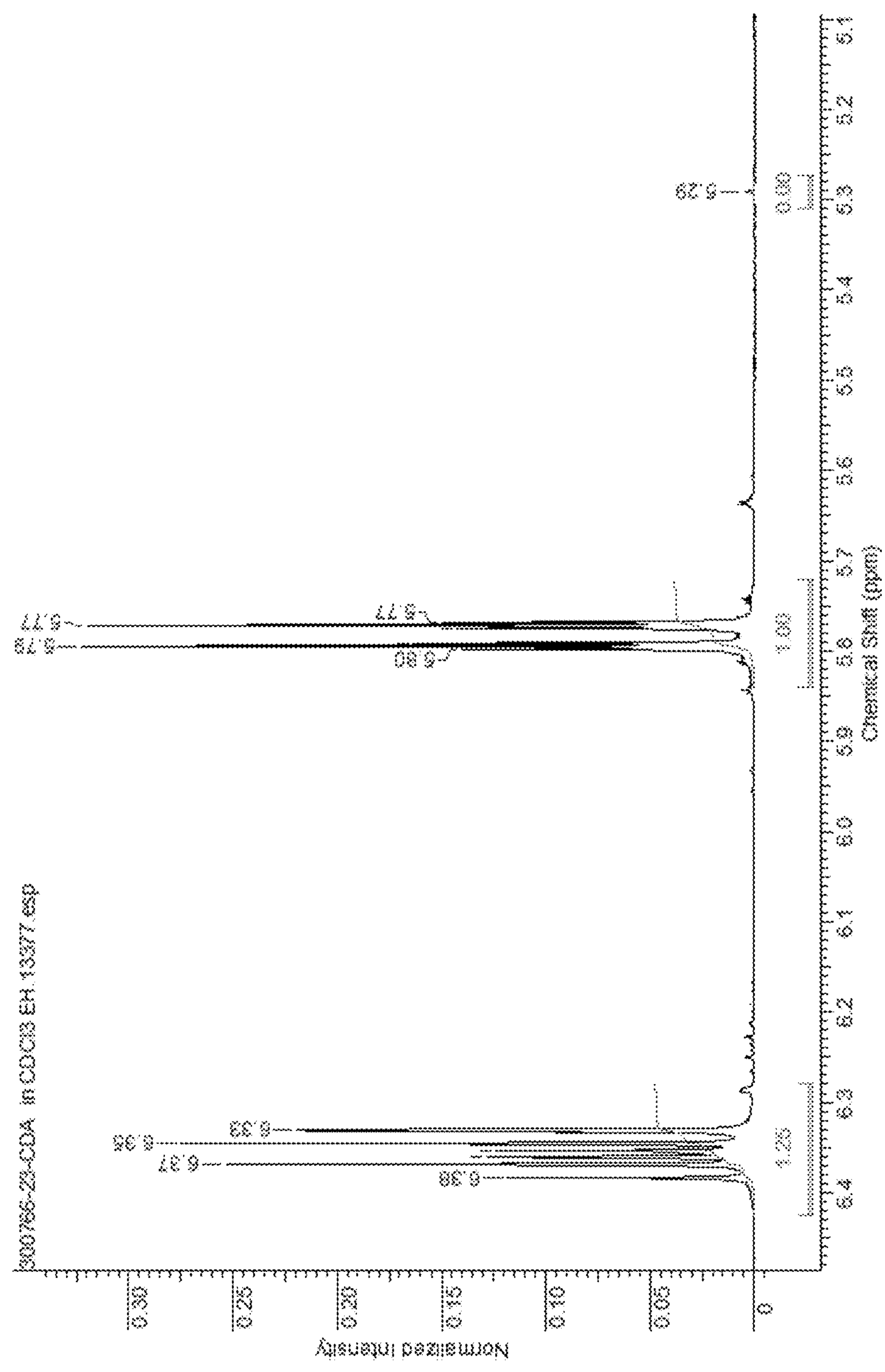
Figure 1C:
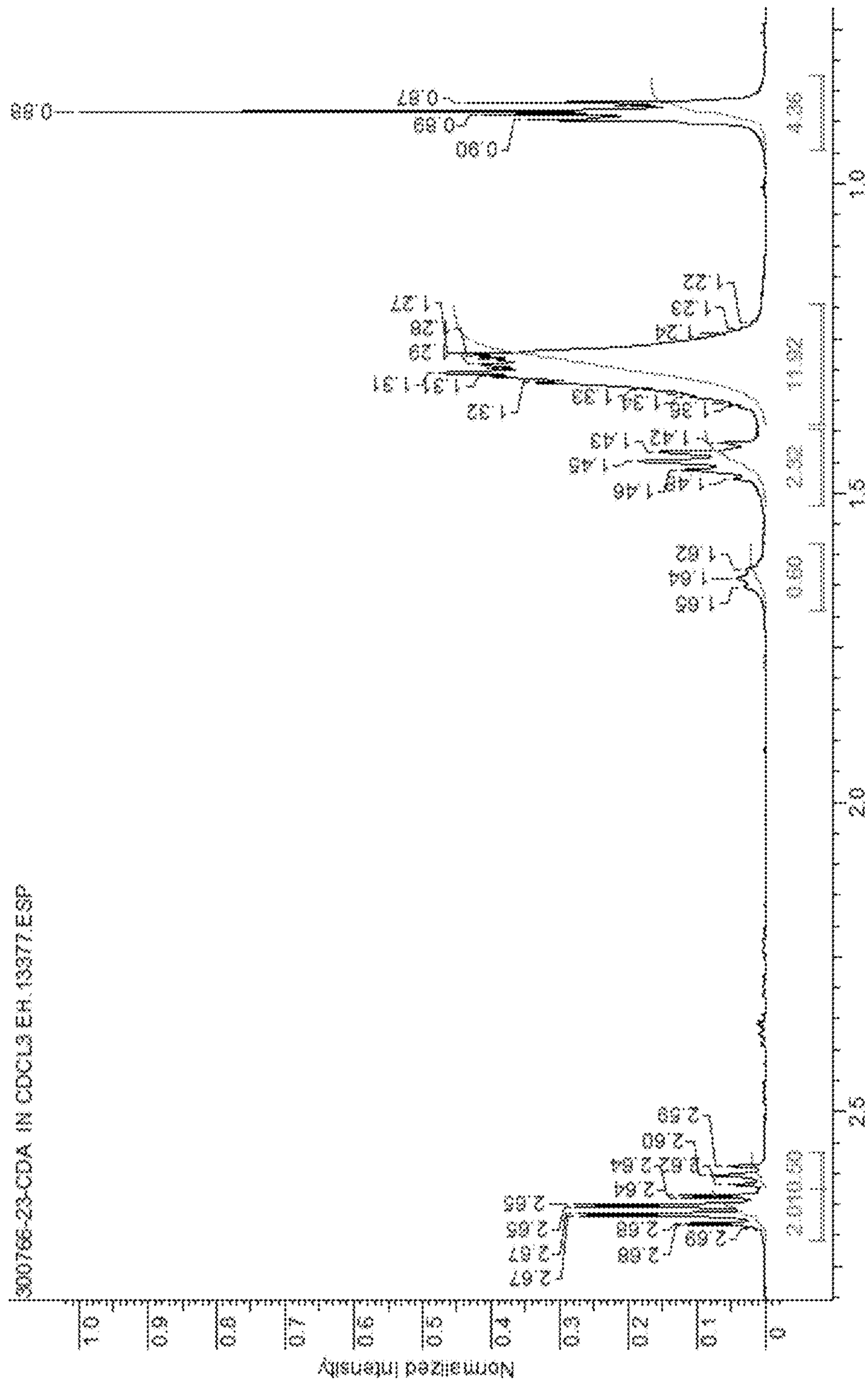

Evaporation of the DCM and lights from the wet CDA under vacuum (at $T_B$=50° C.) gave crude CDA (50.5 g), which was analysed by GC and $^1$H-NMR (see FIGS. 1A, 1B and 1C for $^1$H-NMR spectra). The calculated yield of crude CDA was ~68%, based on 1,3-DBD, or 46.8%, based on 2-decanone.

The purity of the crude CDA obtained was 88.2% (by GC area %). The main impurity in the crude product was 2-bromomethylidene nonanoic acid (BMNA): 8.8% (by GC, area %).

Example 2

Preparation of Cis-2-Decenoic Acid

Step 1:

Into a mixture of 2-decanone (400 g, 2.564 mol) and aq. 48% HBr (600 g), stirred and cooled to ~10° C., was added bromine (800 g, 5 mol), dropwise over 5 h. The reaction started immediately with the start of the addition of the bromine and no accumulation of bromine was observed. The reaction was exothermic and accompanied by the emission of HBr gas, just before the end of the addition of the bromine, which was absorbed in a scrubber.

Most of the reaction took place during the addition of the bromine, and after standing overnight at room temperature, without stirring, the composition of the reaction mixture stabilized. Partial conversion of the 3,3-dibromo-2-decanone (3,3-DBD) to the desired product, 1,3-dibromo-2-decanone (1,3-DBD), took place. To the reaction mixture was added water (300 g) at RT, with stirring for 30 min, and the phases were separated.

An aqueous phase (1207 g) was obtained containing ~49.5% HBr (d=1.51 g/ml) and crude DBD (789 g, d=1.42 g/ml). The concentration of 1,3-DBD in the crude product was 70.4% (GC, area %).

Step 2:

An aqueous solution of $K_2CO_3$, in a concentration of 25% w/w, was prepared in a 2 L stirred reactor by the batchwise addition of $K_2CO_3$ (400 g) to water (1200 g). The reaction was exothermic. To this solution was added a part of the aqueous phase of the reaction mixture of CDA-K (50 g) remaining from a previous run. The clear solution obtained was heated to 40° C. and crude DBD (Step 1, 400 g) was added to it dropwise over 70 min. The progress of the reaction was monitored by GC and by the change in the pH. The reaction was completed by cooking at 40° C. for 1.0 h, then at 50° C. for 2.0 h, with mechanical stirring.

The end of the reaction was determined by the pH (drop in the pH from 12.7 to 9.6) and by GC analysis of the reaction mixture (disappearance of 1,3-DBD to ≤1%, area %). After completion of the reaction, cooling to RT and stopping the stirring, an organic phase appeared above the aqueous phase which contained unreacted 3-BD and 3,3-DBD, and by-products formed by a condensation reaction of crude DBD. The phases were separated. 50 g of the aq. phase was taken for use in the next run.

In order to reduce the amount of impurities to a minimum, the aqueous phase (1943 g) was washed three times with dichloromethane (DCM, 3×500 g).

After the washing stage, an aqueous phase was obtained containing cis-2-decenoic acid potassium salt (CDA-K), organic by-products, KBr and $KHCO_3$. In order to obtain the crude cis-2-decanoic acid (CDA), the aqueous phase was acidified by the dropwise addition of aq. 32% HCl (401 g) over 1 h. During the acidification (final pH=1.9), $CO_2$ (calculated at 127 g) was emitted.

After stopping the stirring, an aqueous phase (2017 g) was obtained containing salts: KCl and KBr (heavy phase, d=1.19 g/ml) and wet crude CDA (light phase, 128 g, d=1.03 g/ml).

Figure 2A:
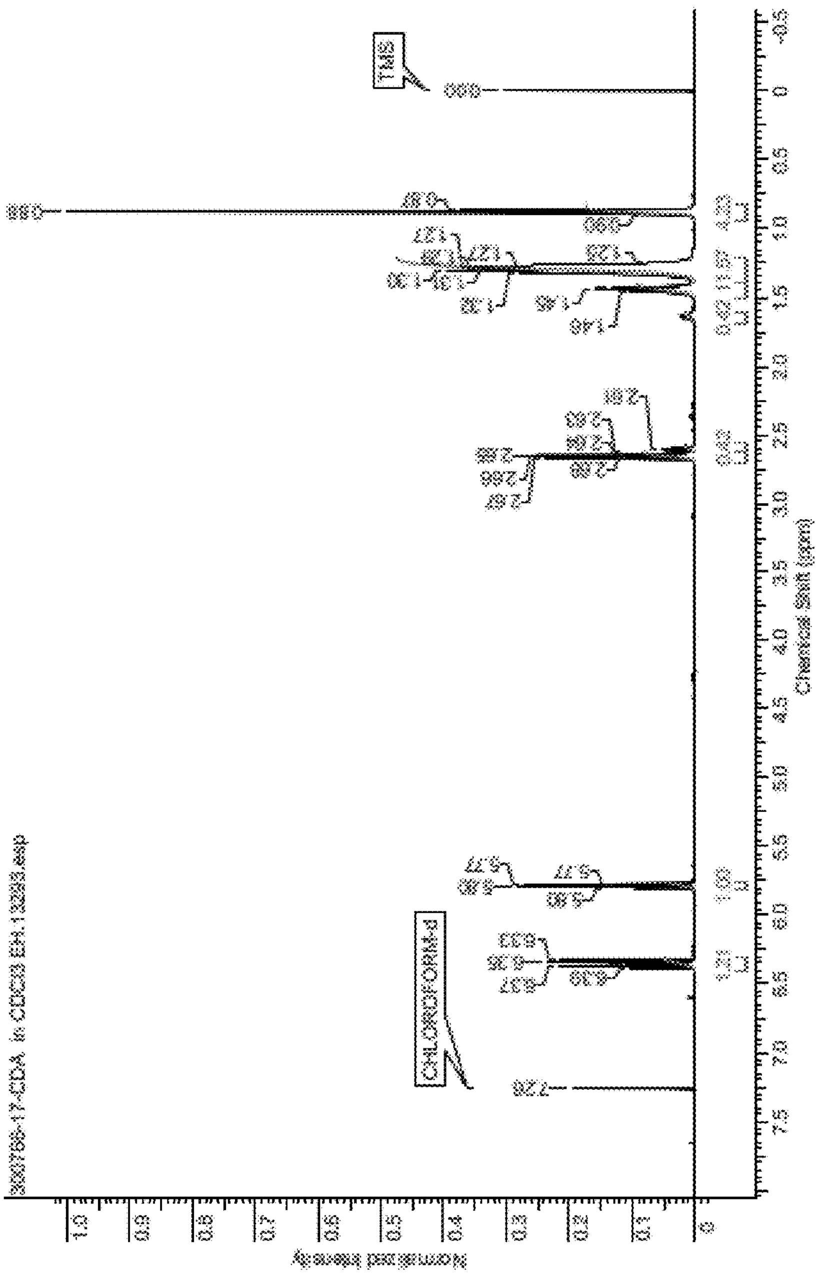
FIGS. 2A, 2B and 2C are $^1$H-NMR spectra of CDA of Example 2.
Figure 2B:
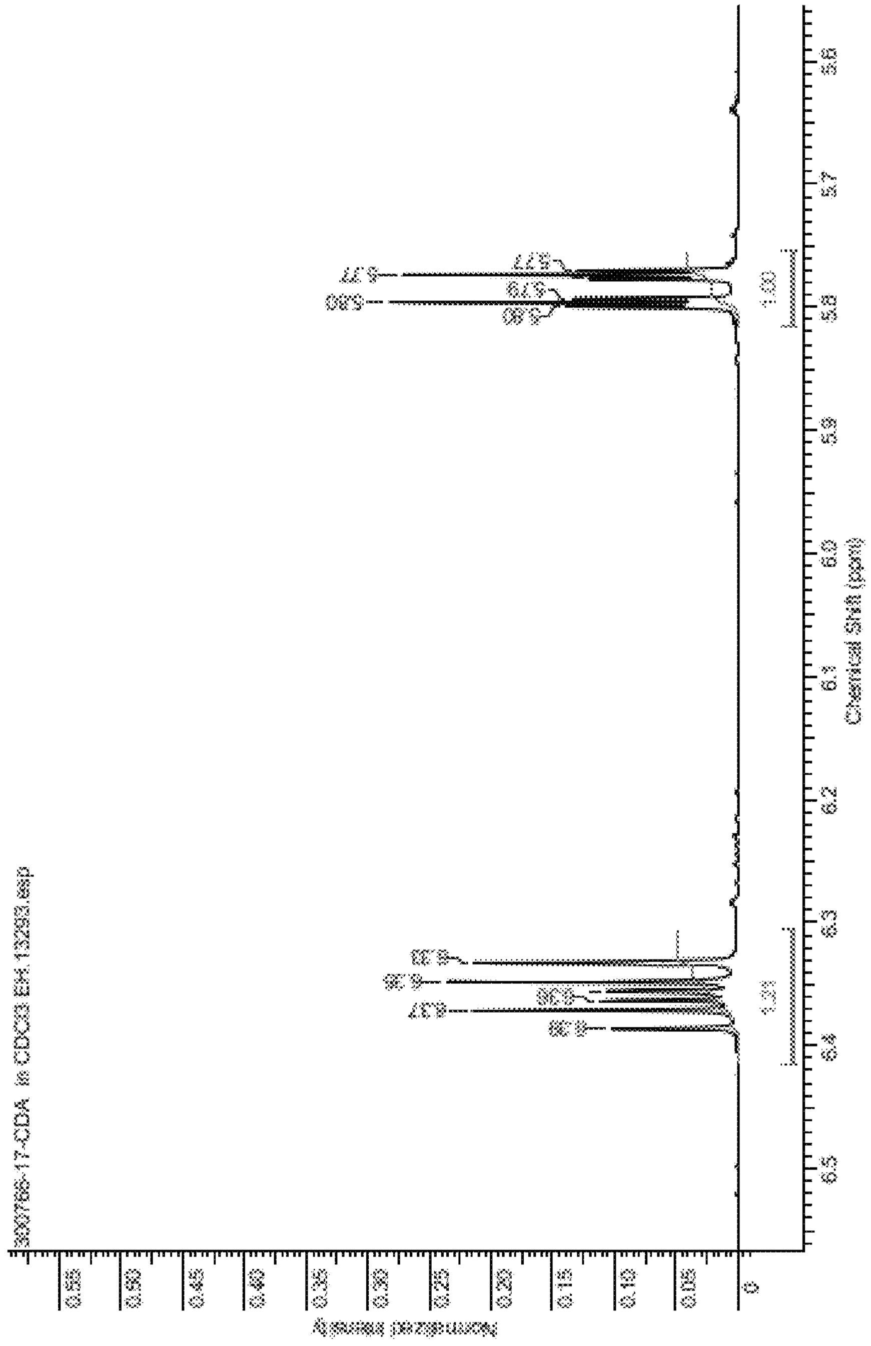
Figure 2C:
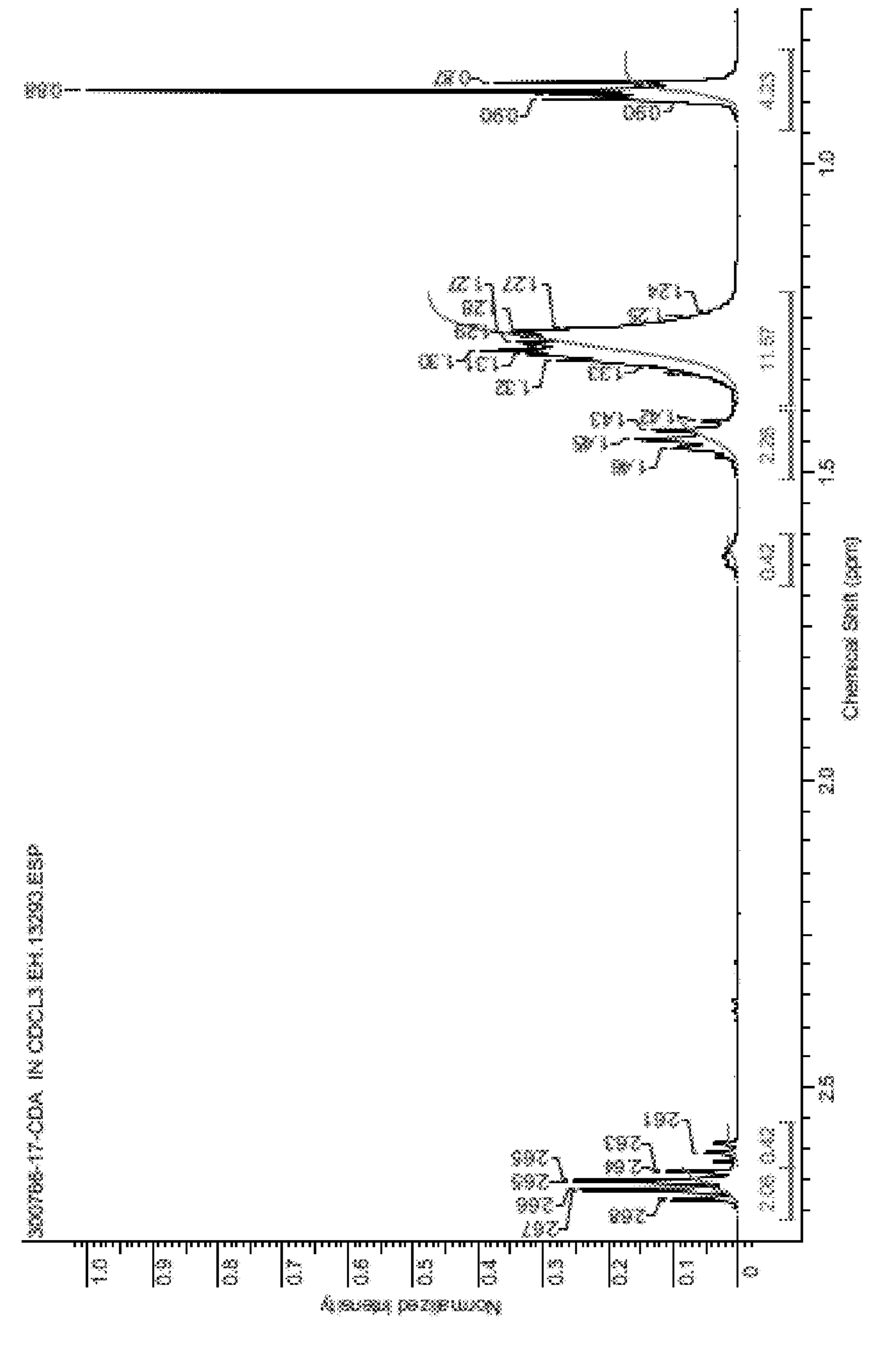

Evaporation of the DCM and lights from the wet CDA under vacuum ($T_B$=50° C.) gave crude CDA (102 g), which was analyzed by GC, HPLC and $^1$H-NMR ($^1$H-NMR spectra in FIGS. 2A, 2B and 2C).

Based on the results, the purity of the crude CDA obtained was 89.7% (by GC area %) and 90.0% (by HPLC, area %). The calculated yield of crude CDA was ~67% based on 1,3-DBD.

Example 3 (Comparative)

Preparation of cis-2-decenoic acid

Step 1 was carried out as in Example 1. The rearrangement reaction of Step 2, however, was carried out without the addition of the alkali metal salt of cis-2-alkenoic acid.

Step 2:

An aqueous solution of $K_2CO_3$, in a concentration of 25% w/w, was prepared in a 1 L stirred reactor by the batchwise addition of $K_2CO_3$ (200 g) to water (600 g). The reaction was exothermic. The clear solution obtained was heated to 40° C. and crude DBD (200 g; obtained as previously described) was added to it dropwise over 60 min. The progress of the reaction was monitored by GC and by the change in the pH.

The mixture of aq. $K_2CO_3$ and crude DBD was stirred for 3 h at a temperature of 50° C. Based on the pH (unchanged at ~13) and on GC, it was seen that no reaction had taken place.

Then suddenly, the temperature in the reactor started to rise spontaneously and reached 76° C. within ten minutes. The end of the reaction was determined by the pH (drop in the pH from 13.3 to 9.5) and by GC analysis of the reaction mixture (disappearance of 1,3-DBD to ≤1%, area %). The phases were separated, and 50 g of the aqueous phase was taken for use in the next run (i.e., the procedure of Example 1).

Example 4

Preparation of Cis-2-Undecenoic Acid

Step 1:

Into a mixture of 2-undecanone (218 g, 1.28 mol) and aq. 48% HBr (300 g), stirred and cooled to ~10° C., was added bromine (410 g, 2.56 mol), dropwise over 3 h. The reaction started immediately with the start of the addition of the bromine and no accumulation of bromine was observed. The reaction was exothermic and accompanied by the emission of HBr gas, just before the end of the addition of the bromine, which was absorbed in a scrubber.

Most of the reaction took place during the addition of the bromine and cooking at room temperature (~20° C.) for 3.5 hours. After standing overnight (~16.5 h) at room temperature, without stirring, the composition of the reaction mixture stabilized. Partial conversion of the 3,3-dibromo-2-undecanone (3,3-DBUD) to the desired product, 1,3-dibromo-2-undecanone (1,3-DBUD), took place. To the reaction mixture was added water (160 g) at RT, with stirring for 30 min, and the phases were separated.

An aqueous phase (627 g) was obtained containing ~50% HBr (d=1.50 g/ml) and crude DBUD (415 g, d=1.39 g/ml). The concentration of 1,3-DBUD in the crude product was 69.1% (GC, area %).

Step 2:

An aqueous solution of $K_2CO_3$, in a concentration of 25% w/w, was prepared in a 1 L stirred reactor by the batchwise addition of $K_2CO_3$ (200 g) to water (600 g). The reaction was exothermic. The clear solution obtained was heated to 40° C. and crude DBUD of Step 1 (200 g) was added to it dropwise over 20 min. The progress of the reaction was monitored by GC and by the change in the pH.

The mixture of aq. $K_2CO_3$ and crude DBUD was stirred for 1 h at a temperature of 50° C., for 1.5 h at a temperature of 60° C., and for an additional 1.5 h at a temperature of 70° C. Based on the pH (unchanged at ~13) and on GC, it was seen that no reaction had taken place.

Next, to the reaction mixture was added a part of the aqueous phase of the reaction mixture of CDA-K (~10 g) dropwise over 15 min. At the end of the addition, the temperature in the reactor started to rise and reached 82° C. within 10 min. This mixture was then stirred for an additional 2 h at 70° C.

The end of the reaction was determined by the pH (drop in the pH from 13 to 10) and by GC analysis of the reaction mixture (disappearance of 1,3-DBUD to ≤1%, area %).

In order to reduce the amount of impurities to a minimum, the reaction mixture (960 g) was washed three times with dichloromethane (DCM, 3×250 g) at RT. It should be mentioned that the first phase separation was slow.

After the washing stage, an aqueous phase was obtained containing cis-2-undecenoic acid potassium salt (CUDA-K), organic by-products, KBr and $KHCO_3$. In order to obtain the crude cis-2-undecenoic acid (CUDA), the aqueous phase was acidified by the dropwise addition of aq. 32% HCl (132 g) over 1 h. During the acidification, $CO_2$ was emitted.

Figure 3A:
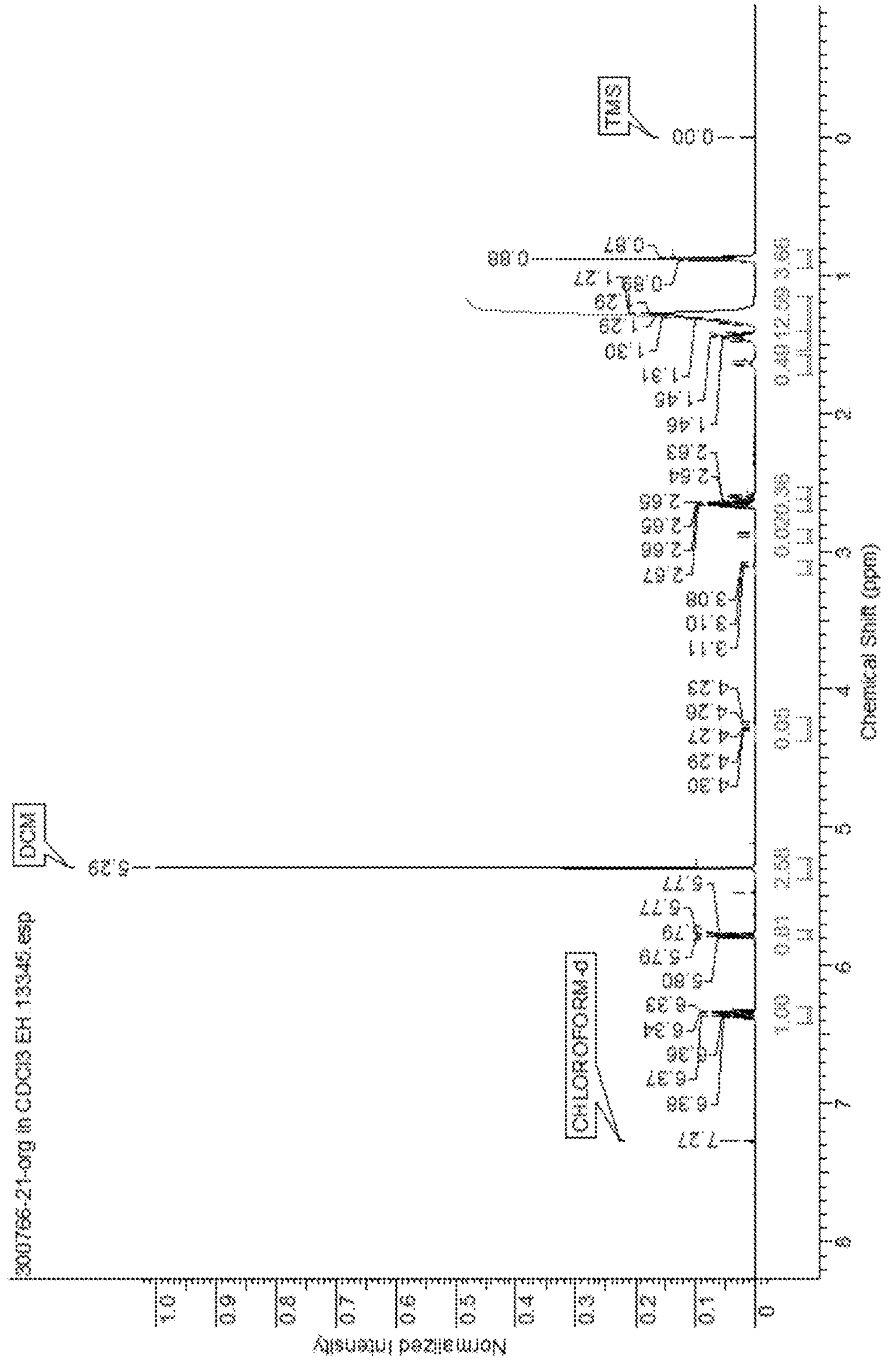
FIGS. 3A, 3B and 3C are $^1$H-NMR spectra of CUDA of Example 4.
Figure 3B:
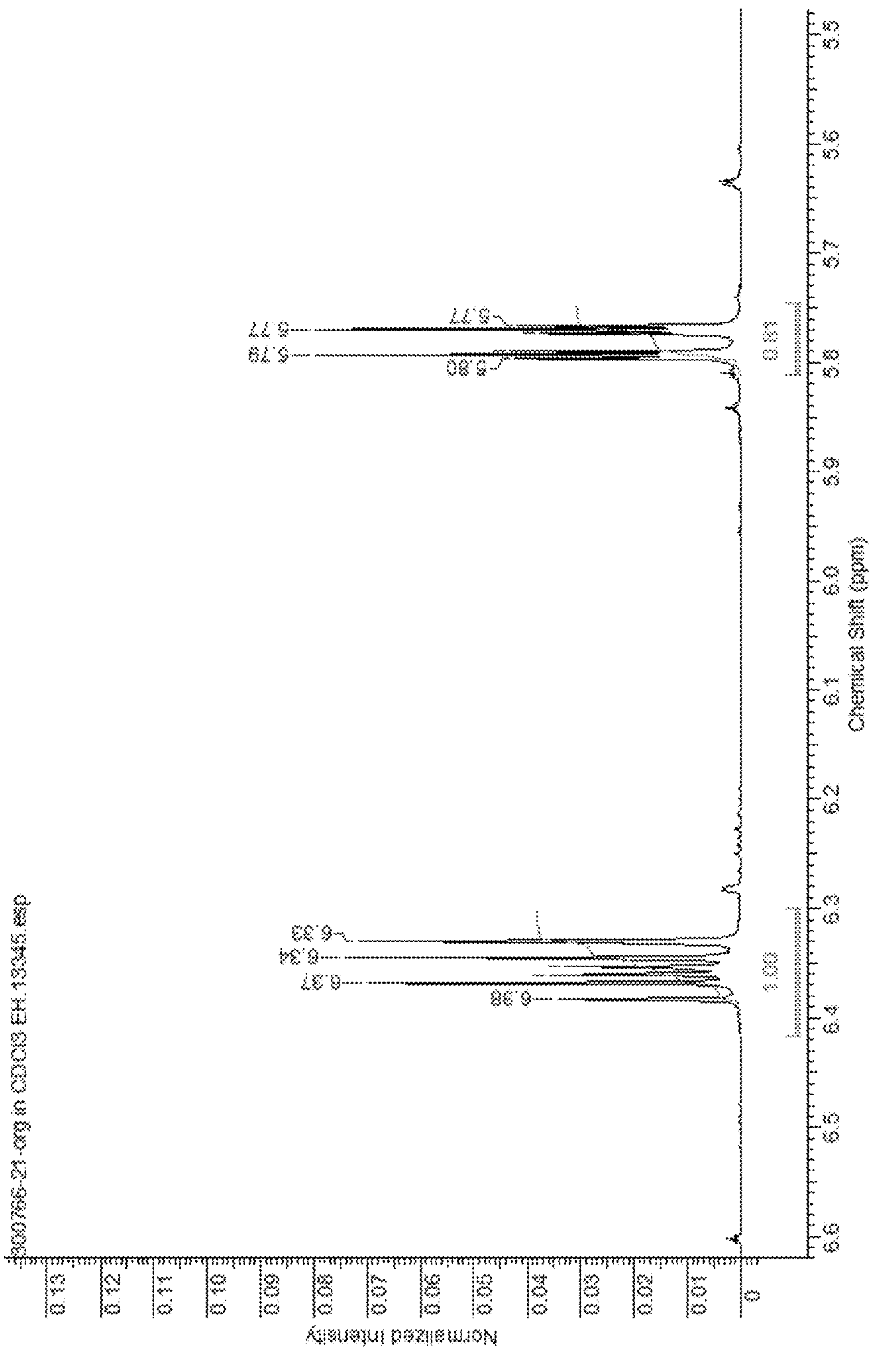
Figure 3C:
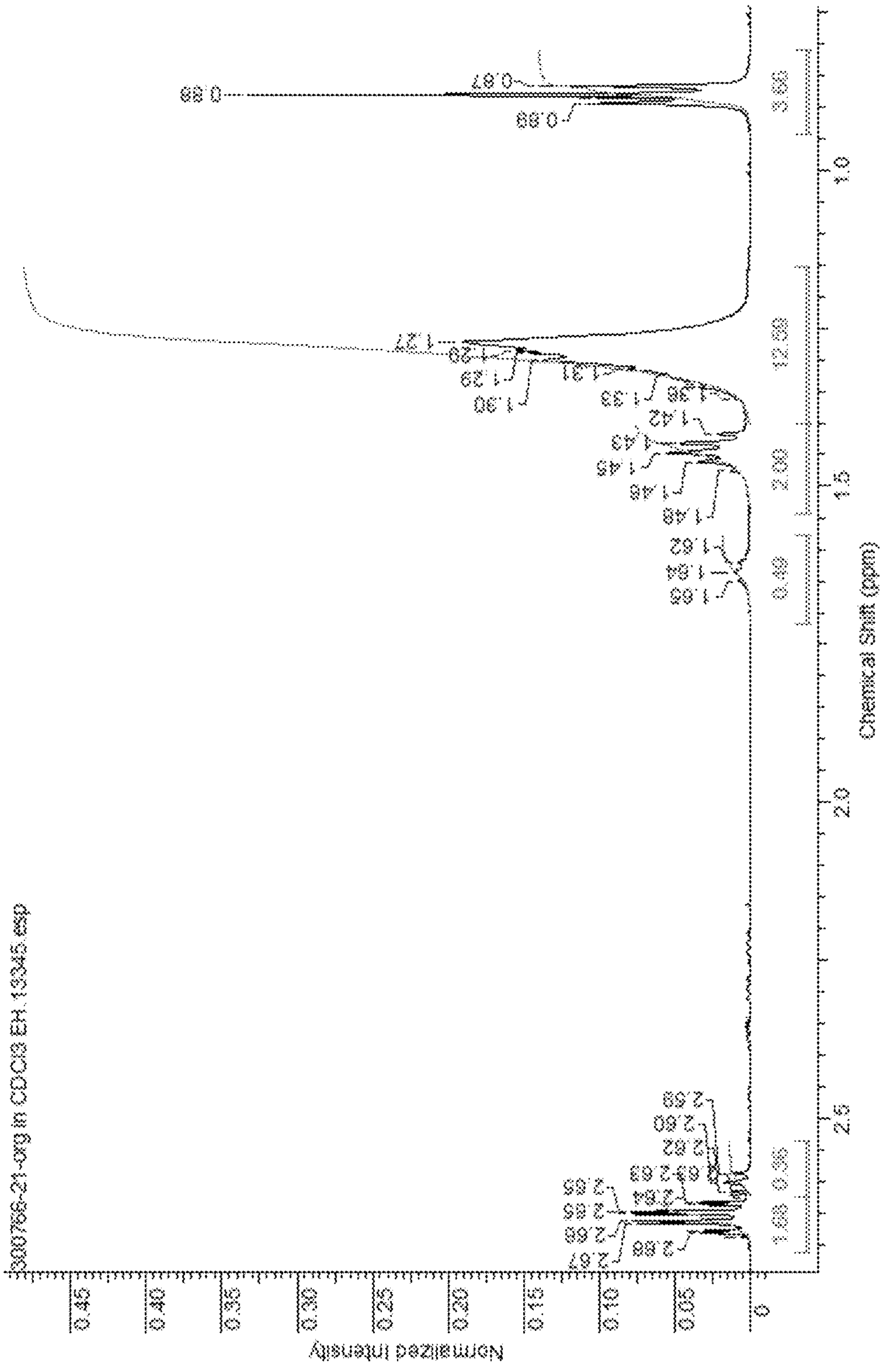

After stopping the stirring, an aqueous phase (762 g) was obtained containing salts: KCl and KBr (heavy phase, d=1.15 g/ml) and wet crude CUDA (light phase, 53 g, d=1.07 g/ml) which was analysed by GC and $^1$H-NMR (see FIGS. 3A, 3B and 3C for $^1$H-NMR spectra). The purity of the crude CUDA obtained was 89.6% (by GC area %). The main impurity in the crude product was 2-bromomethylidene decanoic acid (BMDA): 5.2% (by GC, area %).

Evaporation of the DCM and lights from the wet CUDA under vacuum (at $T_B$=50° C.) gave crude CUDA (35 g).

It is seen that in this Example, a small amount of alkali metal salt of a homologue acid (CDA-K) was used to advance the preparation of CUDA. The aqueous phase obtained containing cis-2-undecenoic acid potassium salt (CUDA-K), with an insignificant amount of CDA-K, can be used to supply, for the next run, a catalytically effective amount of CUDA-K to be added to the alkaline $K_2CO_3$ solution before the slow addition of the crude DBUD starts, to ensure an efficient, manageable reaction.

Example 5 (Comparative)

Preparation of cis-2-nonenoic acid

Step 1:

Into a mixture of 2-nonanone (from Sigma-Aldrich; 182 g, 1.28 mol) and aq. 48% HBr (300 g), stirred and cooled to ~10° C., was added bromine (410 g, 2.56 mol), dropwise over 3 h. The reaction started immediately with the start of the addition of the bromine and no accumulation of bromine was observed. The reaction was exothermic and accompanied by the emission of HBr gas, just before the end of the addition of the bromine, which was absorbed in a scrubber.

Most of the reaction took place during the addition of the bromine and cooking at room temperature (~20° C.) for 2.0 hours. After leaving overnight (~17 h) at room temperature, with stirring, the composition of the reaction mixture stabilized. Partial conversion of the 3,3-dibromo-2-nonanone (3,3-DBN) to the desired product, 1,3-dibromo-2-nonanone (1,3-DBN), took place. To the reaction mixture was added water (160 g) at RT, with stirring for 30 min, and the phases were separated.

An aqueous phase (624 g) was obtained containing ~50% HBr (d=1.50 g/ml) and crude DBN (382 g, d=1.47 g/ml). The concentration of 1,3-DBN in the crude product was 70.6% (GC, area %).

Step 2:

An aqueous solution of $K_2CO_3$, in a concentration of 25% w/w, was prepared in a 1 L stirred reactor by the batchwise addition of $K_2CO_3$ (200 g) to water (600 g). The reaction was exothermic. The clear solution obtained was heated to 46° C. and crude DBN from Step 1 (191 g) was added to it dropwise over 45 min. The progress of the reaction was monitored by the change in the pH and the $T_R$.

Based on the pH (unchanged at ~13) and on GC, it was seen that no reaction had taken place during the addition of the crude DBN. Immediately after the addition of the crude DBN, the pH started to go down and the $T_R$ started to go up.

The end of the reaction was determined by the pH (drop in the pH from 13.3 to 9.1) and by GC analysis of the reaction mixture (disappearance of 1,3-DBN to 1%, area %). The phases were separated. The organic phase (42.6 g) was organic waste.

In order to reduce the amount of impurities to a minimum, the aqueous phase (948 g) was washed three times with dichloromethane (DCM, 3×250 g).

After the washing stage, an aqueous phase was obtained containing cis-2-nonenoic acid potassium salt (CNA-K), organic by-products, KBr and $KHCO_3$. In order to obtain the crude cis-2-nonenoic acid (CNA), the aqueous phase was acidified by the dropwise addition of aq. 32% HCl (227 g) over 1 h. During the acidification, $CO_2$ was emitted.

Figure 4A:
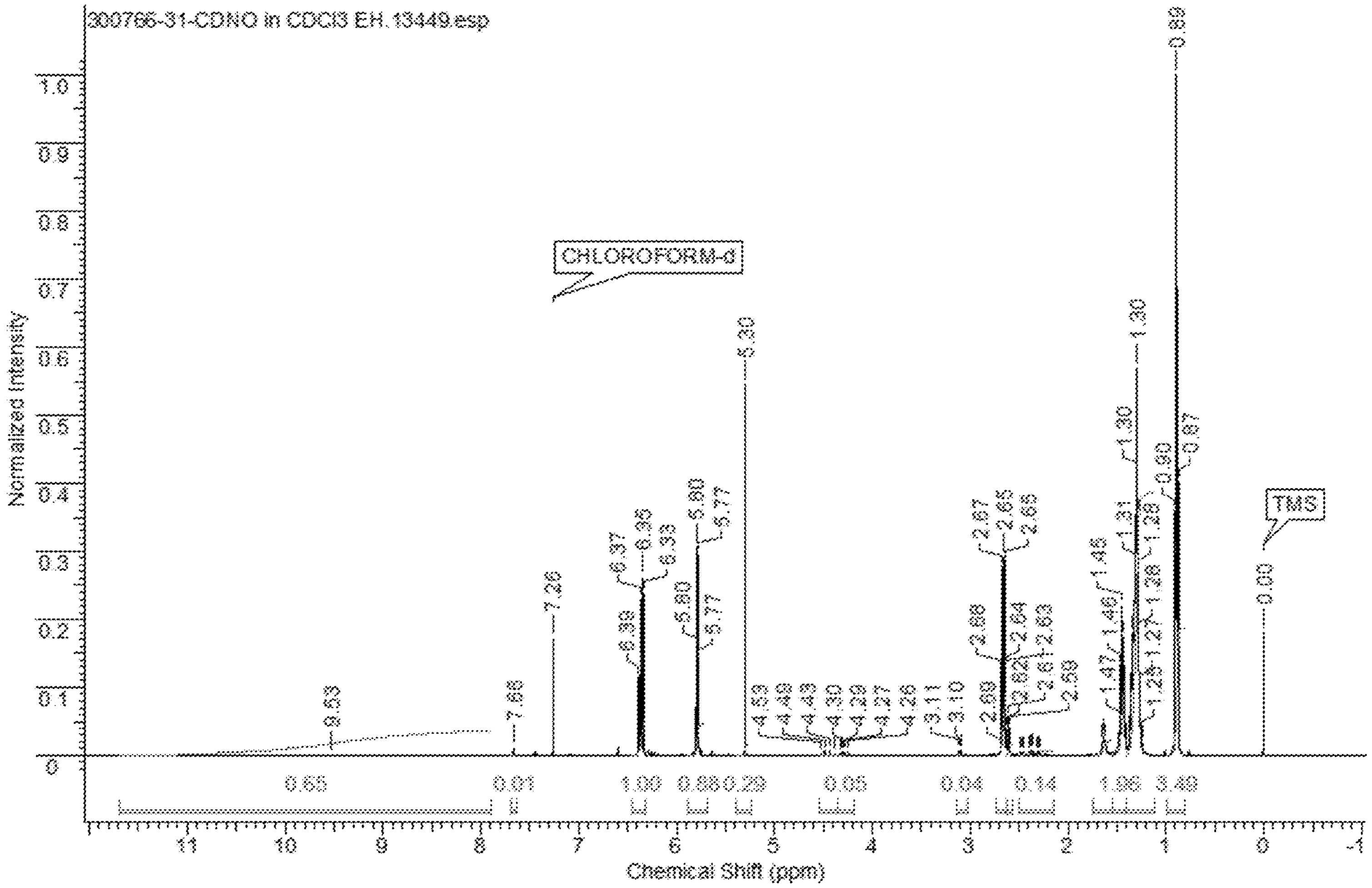
FIGS. 4A, 4B and 4C are $^1$H-NMR spectra of CNA of Example 5.
Figure 4B:
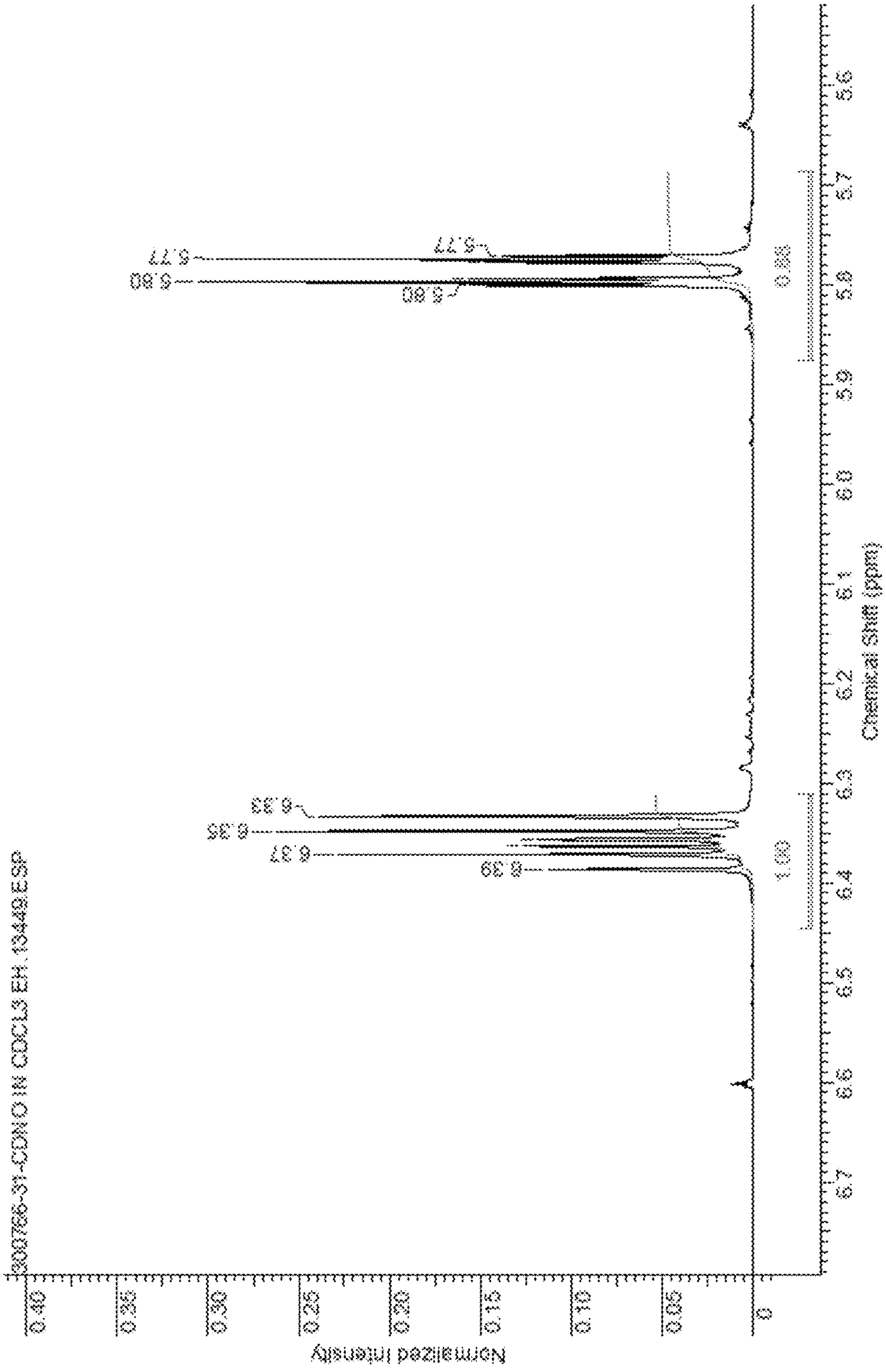
Figure 4C:
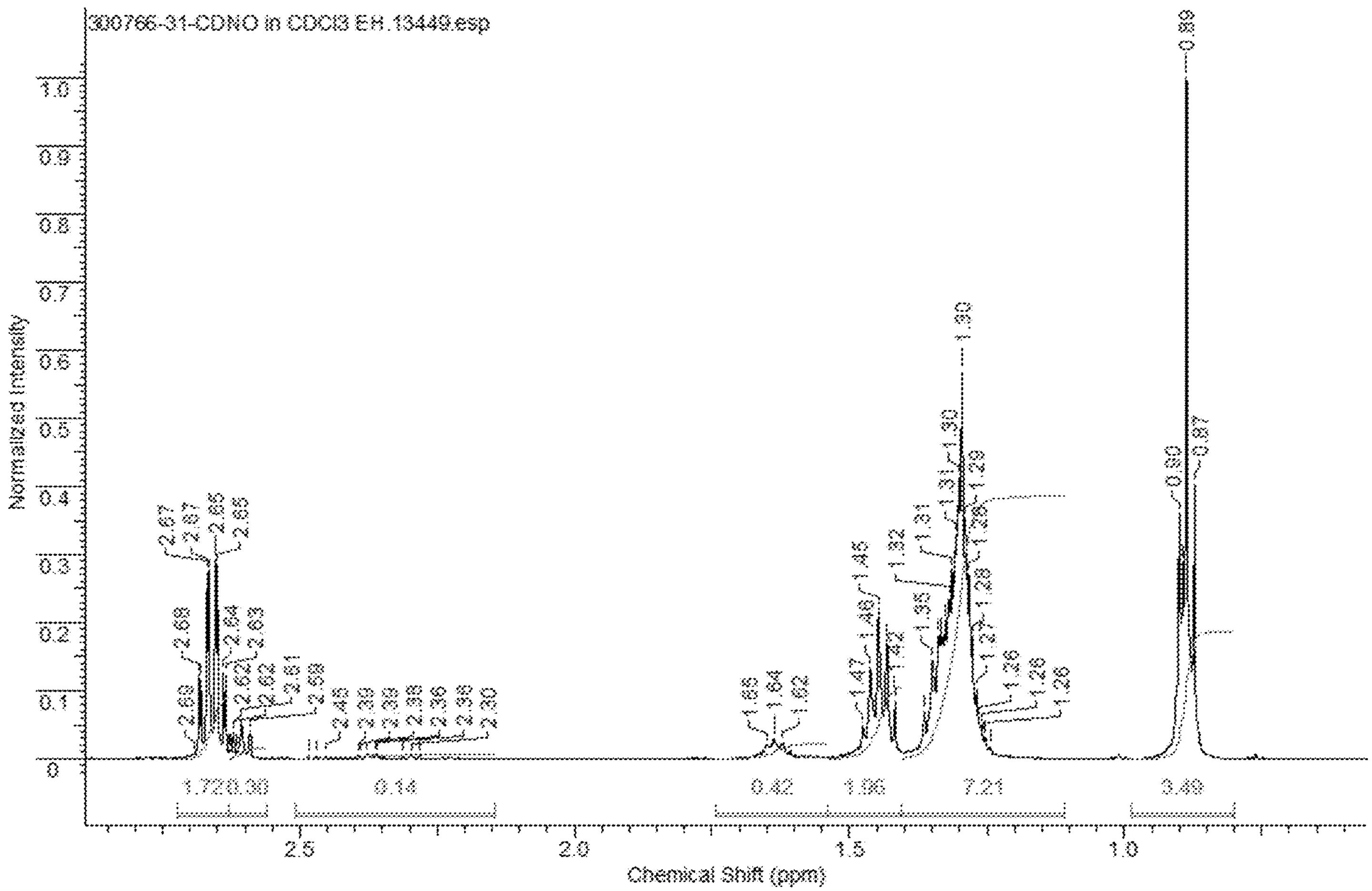

After stopping the stirring, an aqueous phase (978 g) was obtained containing salts: KCl and KBr (heavy phase, d=1.19 g/ml) and wet crude CNA (light phase, 51 g, d=1.02 g/ml) which was analysed by GC and $^1$H-NMR (see FIGS. 4A, 4B and 4C for $^1$H-NMR spectra). The purity of the obtained CNA was 92.0% (by GC, area %).

Evaporation of the DCM and lights from the wet CNA under vacuum (at $T_B$=50° C.) gave crude CNA (46.6 g).

Example 6 (Comparative)

Preparation of cis-2-octenoic acid

Step 1:

Into a mixture of 2-octanone (from Sigma-Aldrich; 164 g, 1.28 mol) and aq. 48% HBr (300 g), stirred and cooled to ~10° C., was added bromine (410 g, 2.56 mol), dropwise over 3 h. The reaction started immediately with the start of the addition of the bromine and no accumulation of bromine was observed. The reaction was exothermic and accompanied by the emission of HBr gas, just before the end of the addition of the bromine, which was absorbed in a scrubber.

Most of the reaction took place during the addition of the bromine and cooking at room temperature (~20° C.) for 2.5 hours. After leaving overnight (~15 h) at room temperature, with stirring, the composition of the reaction mixture stabilized. Partial conversion of the 3,3-dibromo-2-octanone (3,3-DBO) to the desired product, 1,3-dibromo-2-octanone (1,3-DBOO), took place. To the reaction mixture was added water (160 g) at RT, with stirring for 30 min, and the phases were separated.

An aqueous phase (636 g) was obtained containing ~50% HBr (d=1.51 g/ml) and crude DBO (358 g, d=1.54 g/ml). The concentration of 1,3-DBO in the crude product was 71.0% (GC, area %).

Step 2:

An aqueous solution of $K_2CO_3$, in a concentration of 25% w/w, was prepared in a 1 L stirred reactor by the batchwise addition of $K_2CO_3$ (200 g) to water (600 g). The reaction was exothermic. The clear solution obtained was heated to 49° C. and crude DBO from Step 1 (182 g) was added to it dropwise over 1 h. The progress of the reaction was monitored by the change in the pH and the $T_R$.

Based on the pH (unchanged at ~13) and on GC, it was seen that no reaction had taken place during the addition of the crude DBO. Immediately after the addition of the crude DBO, the pH started to go down and the $T_R$ started to go up.

The end of the reaction was determined by the pH (drop in the pH from 13.7 to 9.3) and by GC analysis of the reaction mixture (disappearance of 1,3-DBO to ≤1%, area %).

Before starting the washings, water (75 g) was added to the reaction mixture (982 g). In order to reduce the amount of impurities to a minimum, the reaction mixture was washed four times with dichloromethane (DCM, 4×250 g).

After the washing stage, an aqueous phase was obtained containing cis-2-octenoic acid potassium salt (COA-K), organic by-products, KBr and $KHCO_3$. In order to obtain the crude cis-2-octenoic acid (COA), the aqueous phase was acidified by the dropwise addition of aq. 32% HCl (178 g) over 1 h. During the acidification, $CO_2$ was emitted.

Figure 5A:
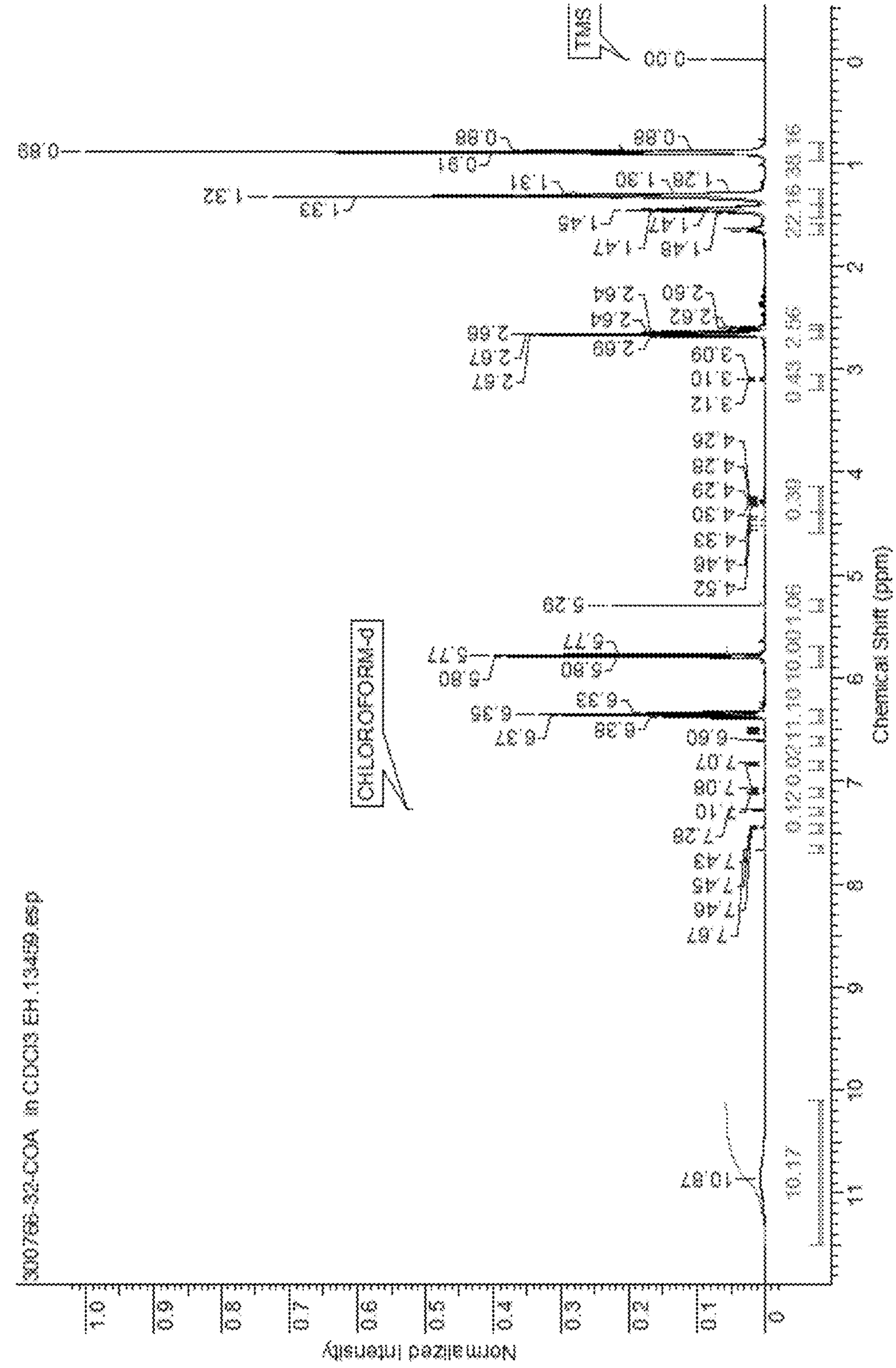
FIGS. 5A, 5B and 5C are $^1$H-NMR spectra of COA of Example 6.
Figure 5B:
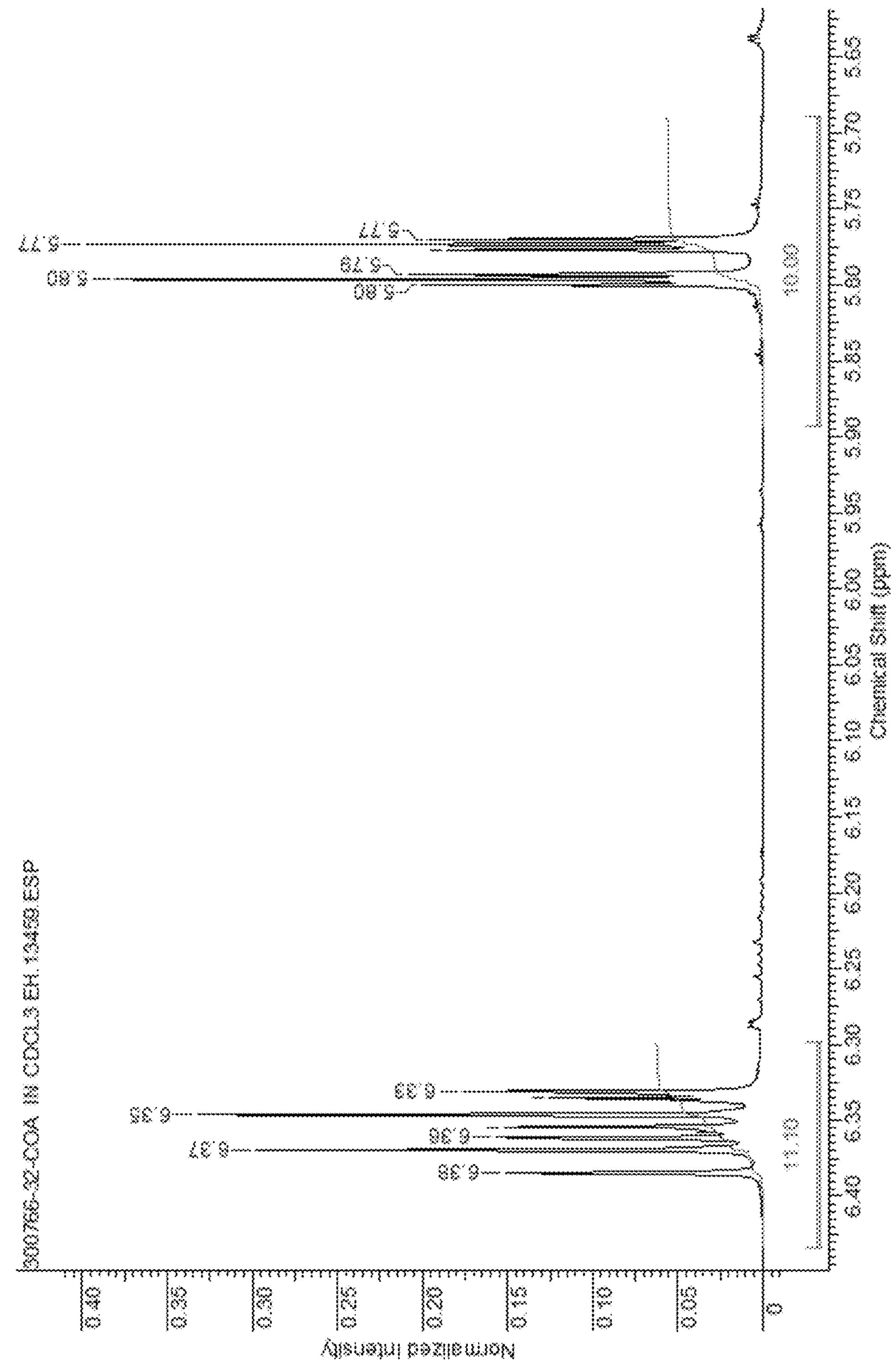
Figure 5C:
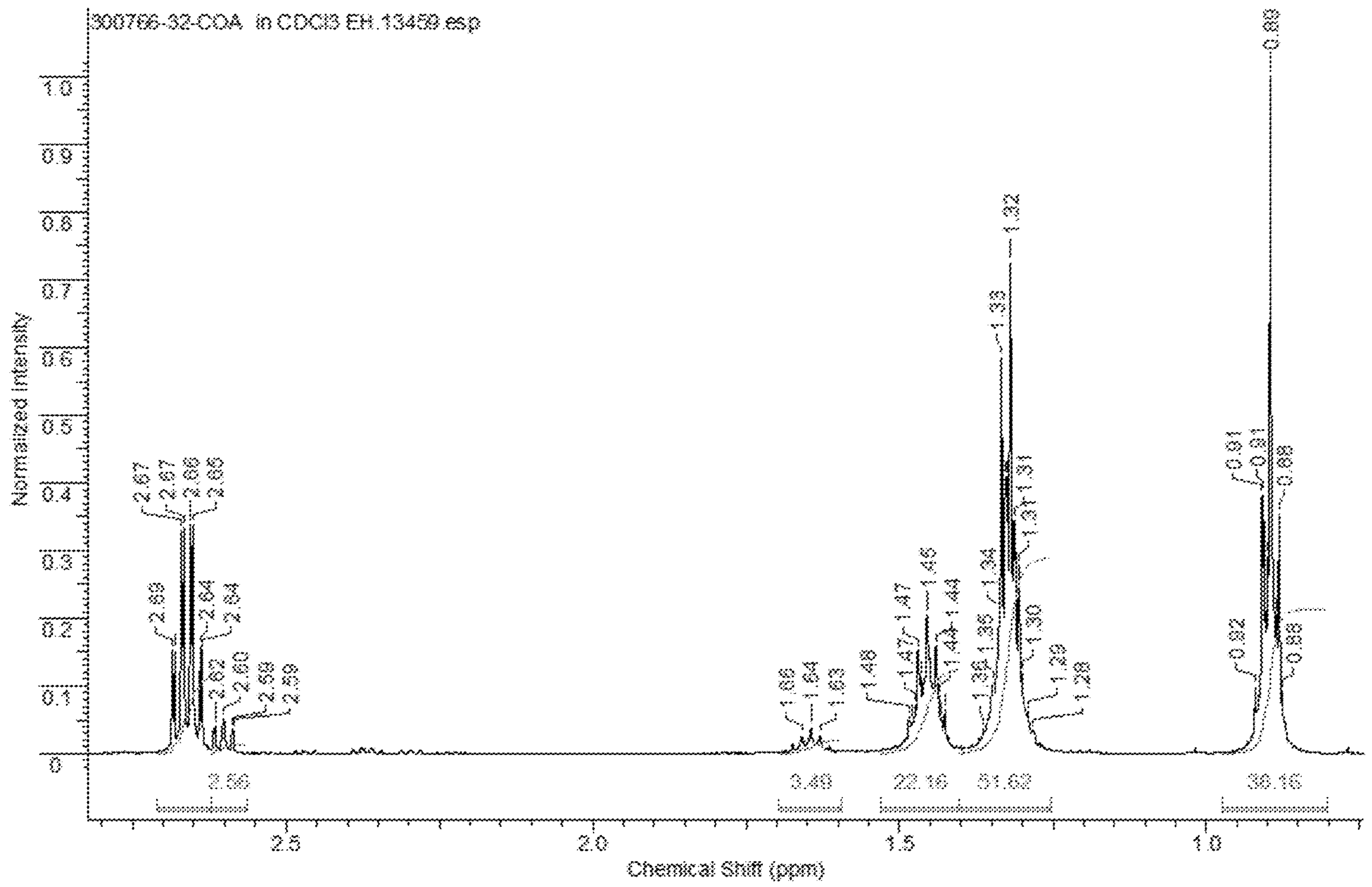

After stopping the stirring, an aqueous phase (938 g) was obtained containing salts: KCl and KBr (heavy phase, d=1.18 g/ml) and wet crude COA (light phase, 44 g, d=1.00 g/ml) which was analysed by GC and $^1$H-NMR (see FIGS. 5A, 5B and 5C for $^1$H-NMR spectra). The purity of the COA obtained was 89.6% (by GC, area %).

Evaporation of the DCM and lights from the wet COA under vacuum (at $T_B$=50° C.) gave crude COA (41.3 g).

Example 7 (Comparative)

Preparation of cis-2-heptenoic acid

Step 1:

Into a mixture of 2-heptanone (from Sigma-Aldrich; 146 g, 1.28 mol) and aq. 48% HBr (300 g), stirred and cooled to ~10° C., was added bromine (410 g, 2.56 mol), dropwise over 3 h. The reaction started immediately with the start of the addition of the bromine and no accumulation of bromine was observed. The reaction was exothermic and accompanied by the emission of HBr gas, just before the end of the addition of the bromine, which was absorbed in a scrubber.

Most of the reaction took place during the addition of the bromine and cooking at room temperature (~20° C.) for 4.5 hours. After standing overnight (~17 h) at room temperature, with stirring, the composition of the reaction mixture stabilized. Partial conversion of the 3,3-dibromo-2-heptanone (3,3-DBH) to the desired product, 1,3-dibromo-2-heptanone (1,3-DBH), took place. To the reaction mixture was added water (160 g) at RT, with stirring for 30 min, and the phases were separated.

An aqueous phase (631 g) was obtained containing ~50% HBr (d=1.52 g/ml) and crude DBH (351 g, d=1.60 g/ml). The concentration of 1,3-DBH in the crude product was 72.6% (GC, area %).

Step 2:

An aqueous solution of $K_2CO_3$, in a concentration of 25% w/w, was prepared in a 1 L stirred reactor by the batchwise addition of $K_2CO_3$ (200 g) to water (600 g). The reaction was exothermic. The clear solution obtained was heated to 49° C. and crude DBH from Step 1 (173 g) was added to it dropwise over 1 h. The progress of the reaction was monitored by the change in the pH and the $T_R$.

Based on the pH (unchanged at ~13), it was seen that no reaction had taken place during the addition of the crude DBH. Immediately after the addition of the crude DBH, the pH started to go down and the $T_R$ started to go up.

The end of the reaction was determined by the pH (drop in the pH from 13.5 to 9.3) and by GC analysis of the reaction mixture (disappearance of 1,3-DBH to ≤1%, area %). After completion of the reaction, cooling to RT and stopping the stirring, an organic phase appeared above the aqueous phase which contained unreacted 3-BH and 3,3-DBH, and by-products formed by a condensation reaction of crude DBH. The phases were separated. The organic phase (24 g) is organic waste.

Before starting the washings, water (50 g) was added to the reaction mixture (948 g). In order to reduce the amount of impurities to a minimum, the diluted reaction mixture (998 g) was washed three times with dichloromethane (DCM, 3×250 g).

After the washing stage, an aqueous phase was obtained containing cis-2-heptenoic acid potassium salt (CHA-K), organic by-products, KBr and $KHCO_3$. In order to obtain the crude cis-2-heptenoic acid (CHA), the aqueous phase was acidified by the dropwise addition of aq. 32% HCl (193 g) over 1 h. During the acidification, $CO_2$ was emitted.

Figure 6A:
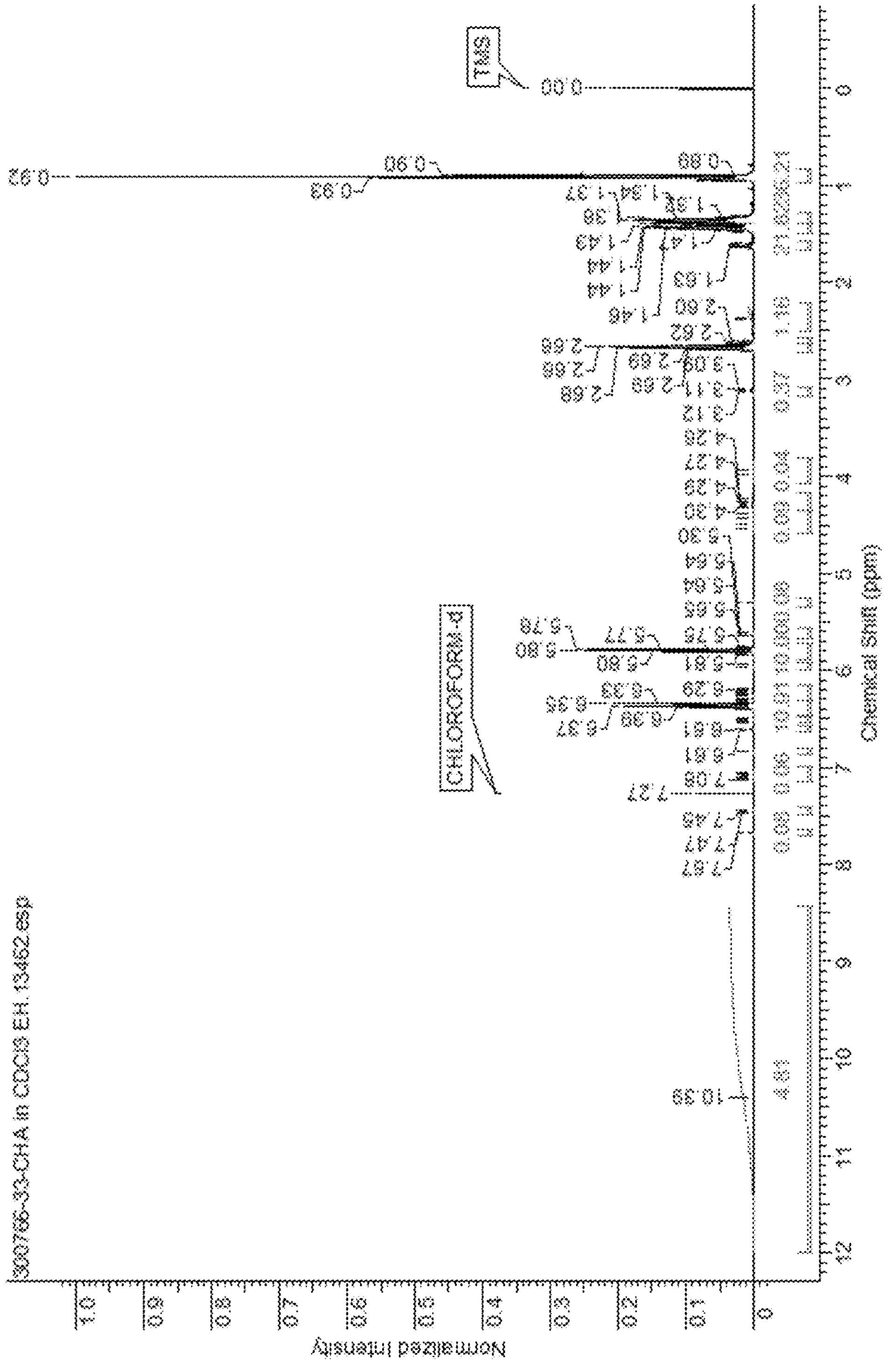
FIGS. 6A, 6B and 6C are $^1$H-NMR spectra of CHA of Example 7.
Figure 6B:
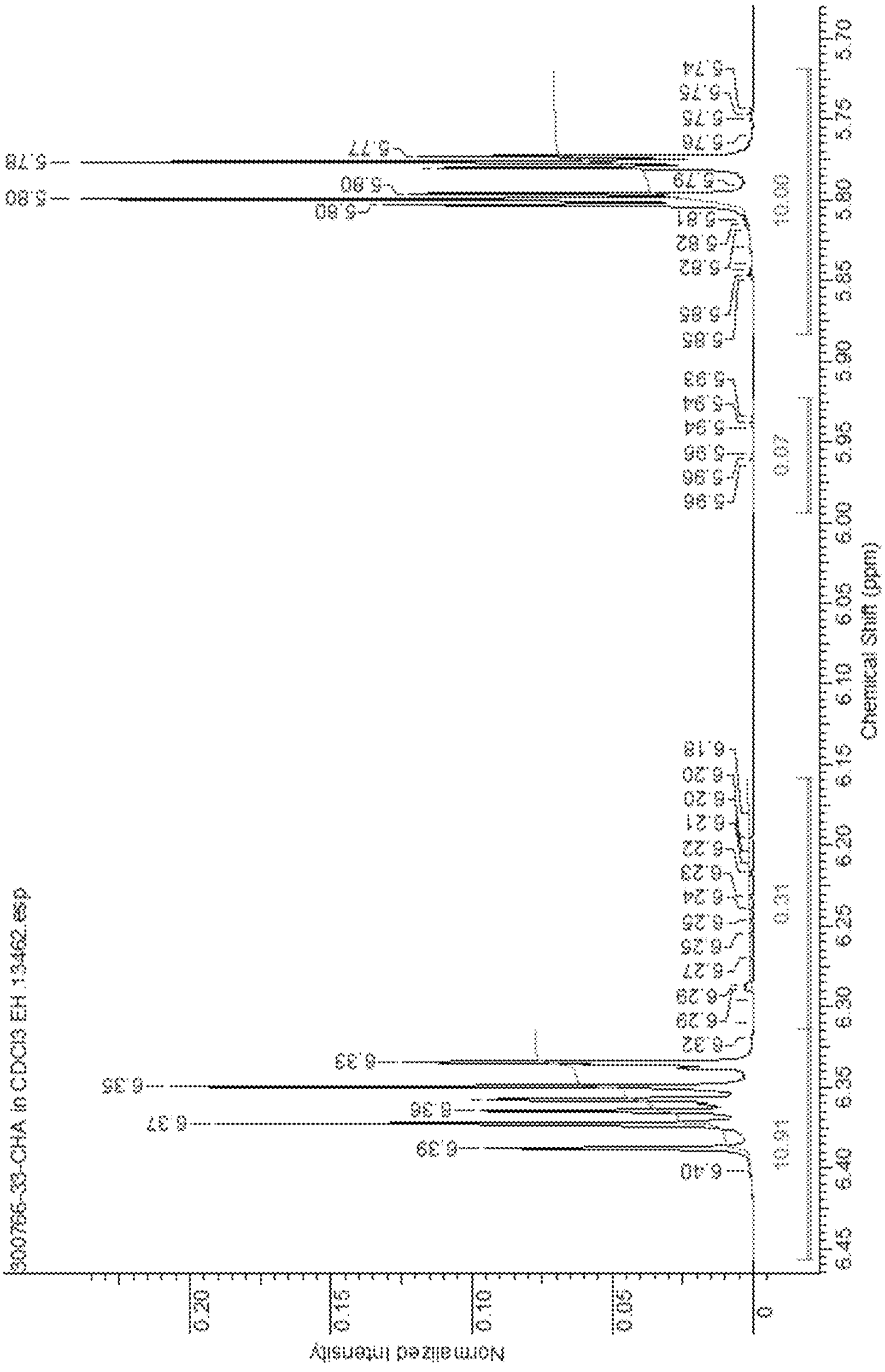
Figure 6C:
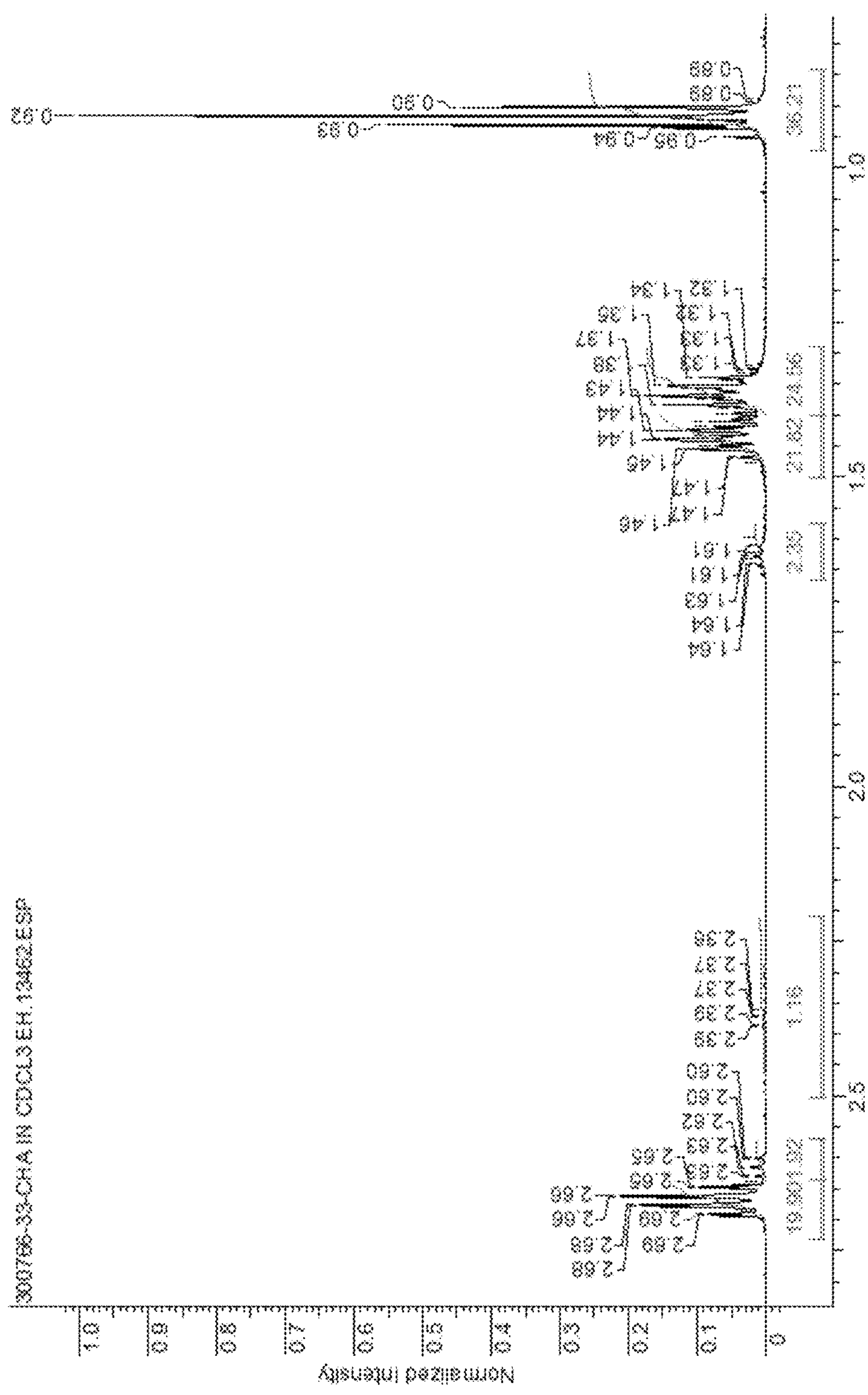

After stopping the stirring, an aqueous phase (1014 g) was obtained containing salts: KCl and KBr (heavy phase, d=1.18 g/ml) and wet crude CHA (light phase, 45 g, d=1.00 g/ml) which was analysed by GC and $^1$H-NMR (see FIGS. 6A, 6B and 6C for $^1$H-NMR spectra). The purity of the CHA obtained was 95.6% (by GC, area %).

Evaporation of the DCM and lights from the wet CHA under vacuum (at $T_B$=50° C.) gave crude CHA (44 g).

The invention claimed is:

1. A process for the preparation of cis-2-alkenoic acid or an alkali metal salt thereof, wherein the cis-2-alkenoic acid is of the formula R—CH═CH—COOH wherein R is a straight alkyl chain $CH_3$-$(CH_2)_n$—, with 3≤n≤10, comprising rearranging a corresponding 1,3-dibromo-2-alkanone in an alkaline environment in the presence of a catalytically effective amount of an alkali metal salt of the cis-2-alkenoic acid, supplied by addition of the cis-2-alkenoic acid or its salt at the beginning of the rearrangement reaction, and isolating from the reaction mixture the cis-2-alkenoic acid, either in the form of the free acid or in the form of the alkali metal salt.

2. A process according to claim 1, comprising gradually adding the 1,3-dibromo-2-alkanone to a reaction vessel which was previously charged with an alkaline aqueous solution of $Na_2CO_3$, $K_2CO_3$, or a mixture thereof and a catalytically effective amount of an alkali metal salt of cis-2-alkenoic acid, at elevated temperature.

3. A process according to claim 1, comprising separating the reaction mixture into aqueous and organic phases, and working-up the aqueous phase, to recover therefrom cis-2-alkenoic acid, either in the form of the free acid or in the form of the alkali metal salt.

4. A process according to claim 3, wherein the aqueous phase is worked-up by washing with an organic solvent, followed by phase separation, to obtain a purified aqueous phase.

5. A process according to claim 1, wherein the reaction mixture is optionally diluted with water and washed with an organic solvent, followed by phase separation, to obtain a purified aqueous phase.

6. A process according to claim 4, further comprising acidifying the purified aqueous phase to obtain a biphasic medium, comprised of a heavy, salt-containing aqueous phase, and a light organic phase consisting essentially of the cis-2-alkenoic acid in the form of the free acid.

7. A process according to claim 1, wherein the 1,3-dibromo-2-alkanone is selected from the group consisting of:

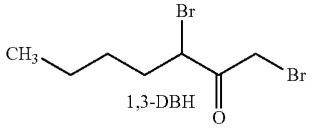

1,3-DBH 1,3-dibromo-2-heptanone

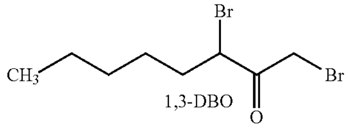

1,3-DBO 1,3-dibromo-2-octanone

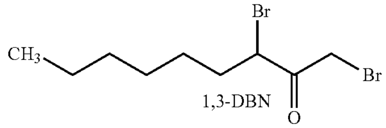

1,3-DBN 1,3-dibromo-2-nonanone

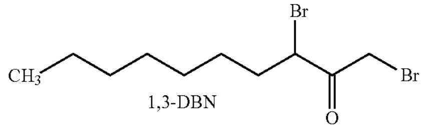

1,3-DBN 1,3-dibromo-2-decanone

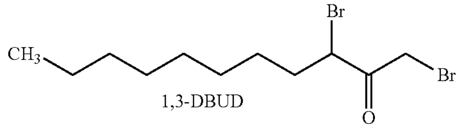

1,3-DBUD 1,3-dibromo-2-undecanone

8. A process according to claim 1, wherein the 1,3-dibromo-2-alkanone, used in the rearrangement reaction, is a crude 1,3-dibromo-2-alkanone obtained by the steps of:

brominating the corresponding 2-alkanone in concentrated hydrobromic acid by the addition of elemental bromine, whereby 1,3-dibromo-2-alkanone is formed in the reaction mixture alongside 3,3-dibromo-2-alkanone;

maintaining the reaction mixture over a hold time adjusted to maximize the interconversion of 3,3-dibromo-2-alkanone to 1,3-dibromo-2-alkanone; and collecting the crude 1,3-dibromo-2-alkanone.

9. A process according to claim 8, wherein the 2-alkanone is selected from the group consisting of 2-heptanone, 2-octanone, 2-nonanone, 2-decanone and 2-undecanone.

10. A process according to claim 8, wherein the hold time is adjusted to reach not less than 65 area % of 1,3-dibromo-2-alkanone measured by gas chromatography.

11. A process according to claim 1, wherein the catalytically effective amount of the alkali metal salt of cis-2-alkenoic acid is up to 10 mol % based on 1,3-dibromo-2-alkanone.

12. A process according to claim 3, wherein a minor portion of the aqueous phase is removed before or after the aqueous phase is worked-up, and is used to supply the catalytically effective amount of alkali metal salt of cis-2-alkenoic acid in a rearrangement reaction of the corresponding 1,3-dibromo-2-alkanone.

13. A process according claim 1, wherein the catalytically effective amount of the alkali metal salt of cis-2-alkenoic acid is supplied to the rearrangement reaction in the form of aqueous solution recovered from an earlier rearrangement reaction.

14. A process according to claim 1, wherein the 1,3-dibromo-2-alkanone is 1,3-dibromo-2-decanone, such that the cis-2-alkenoic acid is cis-2-decenoic acid.

* * * * *